(12) United States Patent
Sathaye et al.

(10) Patent No.: US 8,983,602 B2
(45) Date of Patent: *Mar. 17, 2015

(54) METHOD AND APPARATUS TO PERFORM ELECTRODE COMBINATION SELECTION

(71) Applicant: Cardiac Pacemakers, Inc., St. Paul, MN (US)

(72) Inventors: Alok S. Sathaye, Boston, MA (US); M. Jason Brooke, Woodstock, MD (US); Bruce A. Tockman, Scandia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/085,398

(22) Filed: Nov. 20, 2013

(65) Prior Publication Data

US 2014/0074177 A1   Mar. 13, 2014

Related U.S. Application Data

(63) Continuation of application No. 13/595,688, filed on Aug. 27, 2012, now Pat. No. 8,615,297, which is a continuation of application No. 11/890,668, filed on Aug. 7, 2007, now Pat. No. 8,265,736.

(51) Int. Cl.
| | |
|---|---|
| *A61N 1/08* | (2006.01) |
| *A61N 1/37* | (2006.01) |
| *A61N 1/368* | (2006.01) |
| *A61N 1/365* | (2006.01) |

(52) U.S. Cl.
CPC ............ *A61N 1/3704* (2013.01); *A61N 1/3686* (2013.01); *A61N 1/3702* (2013.01); *A61N 1/36514* (2013.01); *A61N 1/371* (2013.01)
USPC .............................................................. 607/9

(58) Field of Classification Search
None
See application file for complete search history.

(56) References Cited

U.S. PATENT DOCUMENTS

| 3,920,005 A | 11/1975 | Gombrich et al. |
|---|---|---|
| 4,023,564 A | 5/1977 | Valiquette et al. |

(Continued)

FOREIGN PATENT DOCUMENTS

| EP | 0468720 A2 | 1/1992 |
|---|---|---|
| EP | 0560569 A2 | 9/1993 |

(Continued)

OTHER PUBLICATIONS

Acar et al., "SVD-Based on-line Exercise ECG Signal orthogonalization," IEEE Transactions on Biomedical Engineering, vol. 46, No. 3, Mar. 1999. Abstract only.

(Continued)

*Primary Examiner* — Brian T Gedeon
(74) *Attorney, Agent, or Firm* — Seager, Tufte & Wickhem, LLC

(57) ABSTRACT

Approaches for selecting an electrode combination of multi-electrode pacing devices are described. Electrode combination parameters that support cardiac function consistent with a prescribed therapy are evaluated for each of a plurality of electrode combinations. Electrode combination parameters that do not support cardiac function are evaluated for each of the plurality of electrode combinations. An order is determined for the electrode combinations based on the parameter evaluations. An electrode combination is selected based on the order, and therapy is delivered using the selected electrode combination.

20 Claims, 12 Drawing Sheets

(56) References Cited

U.S. PATENT DOCUMENTS

| | | |
|---|---|---|
| 4,340,063 A | 7/1982 | Maurer |
| 4,364,396 A | 12/1982 | Barthel |
| 4,365,636 A | 12/1982 | Barker et al. |
| 4,458,692 A | 7/1984 | Simson |
| 4,476,869 A | 10/1984 | Bihn |
| 4,550,221 A | 10/1985 | Mabusth |
| 4,552,154 A | 11/1985 | Hartlaub |
| 4,562,841 A | 1/1986 | Brockway et al. |
| 4,573,481 A | 3/1986 | Bullara et al. |
| 4,648,407 A | 3/1987 | Sackner |
| 4,680,708 A | 7/1987 | Ambos et al. |
| 4,686,332 A | 8/1987 | Greanias et al. |
| 4,827,935 A | 5/1989 | Geddes et al. |
| 4,860,766 A | 8/1989 | Sackner |
| 4,878,497 A | 11/1989 | Callaghan et al. |
| 4,928,688 A | 5/1990 | Mower |
| 4,953,551 A | 9/1990 | Mehra et al. |
| 4,979,507 A | 12/1990 | Heinz et al. |
| 5,000,189 A | 3/1991 | Throne et al. |
| 5,033,467 A | 7/1991 | Bocchi et al. |
| 5,036,849 A | 8/1991 | Hauck et al. |
| 5,101,831 A | 4/1992 | Koyama et al. |
| 5,105,354 A | 4/1992 | Nishimura et al. |
| 5,133,353 A | 7/1992 | Hauser |
| 5,146,918 A | 9/1992 | Kallok |
| 5,170,784 A | 12/1992 | Ramon |
| 5,178,156 A | 1/1993 | Takishima et al. |
| 5,179,945 A | 1/1993 | Van Hofwegen et al. |
| 5,184,615 A | 2/1993 | Nappholz et al. |
| 5,187,657 A | 2/1993 | Forbes et al. |
| 5,203,348 A | 4/1993 | Dahl et al. |
| 5,209,229 A | 5/1993 | Gilli et al. |
| 5,217,021 A | 6/1993 | Steinhaus et al. |
| 5,222,493 A | 6/1993 | Sholder |
| 5,230,337 A | 7/1993 | Dahl et al. |
| 5,233,983 A | 8/1993 | Markowitz |
| 5,261,400 A | 11/1993 | Bardy |
| 5,271,411 A | 12/1993 | Ripley et al. |
| 5,273,035 A | 12/1993 | Markowitz et al. |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck |
| 5,324,310 A | 6/1994 | Greeninger |
| 5,331,966 A | 7/1994 | Bennett et al. |
| 5,331,996 A | 7/1994 | Ziehm |
| 5,333,095 A | 7/1994 | Stevenson et al. |
| 5,334,222 A | 8/1994 | Salo et al. |
| 5,335,657 A | 8/1994 | Terry, Jr. et al. |
| 5,350,410 A | 9/1994 | Kleks et al. |
| 5,353,788 A | 10/1994 | Miles et al. |
| 5,360,442 A | 11/1994 | Dahl et al. |
| 5,366,496 A | 11/1994 | Dahl et al. |
| 5,372,606 A | 12/1994 | Lang |
| 5,374,280 A | 12/1994 | den Dulk |
| 5,376,106 A | 12/1994 | Stahmann |
| 5,376,476 A | 12/1994 | Eylon et al. |
| 5,388,578 A | 2/1995 | Yomtov et al. |
| 5,391,200 A | 2/1995 | Knight |
| 5,397,342 A | 3/1995 | Heil et al. |
| 5,411,031 A | 5/1995 | Yomtov et al. |
| 5,411,525 A | 5/1995 | Swanson et al. |
| 5,411,529 A | 5/1995 | Hudrlik et al. |
| 5,411,533 A | 5/1995 | Dubreuil et al. |
| 5,411,539 A | 5/1995 | Neisz et al. |
| 5,431,693 A | 7/1995 | Schroeppel |
| 5,439,482 A | 8/1995 | Adams et al. |
| 5,441,518 A | 8/1995 | Adams et al. |
| 5,443,485 A | 8/1995 | Housworth et al. |
| 5,447,519 A | 9/1995 | Peterson |
| 5,468,254 A | 11/1995 | Hahn et al. |
| 5,485,851 A | 1/1996 | Erickson |
| 5,517,983 A | 5/1996 | Deighan et al. |
| 5,520,191 A | 5/1996 | Karlsson et al. |
| 5,522,860 A | 6/1996 | Molin et al. |
| 5,531,779 A | 7/1996 | Dahl et al. |
| 5,534,017 A | 7/1996 | van Krieken et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson et al. |
| 5,557,210 A | 9/1996 | Cappa et al. |
| 5,591,216 A | 1/1997 | Testerman et al. |
| 5,603,732 A | 2/1997 | Dahl et al. |
| 5,620,466 A | 4/1997 | Haefner et al. |
| 5,626,620 A | 5/1997 | Kieval |
| 5,634,938 A | 6/1997 | Swanson et al. |
| 5,641,326 A | 6/1997 | Adams |
| 5,650,759 A | 7/1997 | Hittman et al. |
| 5,658,318 A | 8/1997 | Stroetmann et al. |
| 5,662,688 A | 9/1997 | Haefner et al. |
| 5,662,696 A | 9/1997 | Kroll et al. |
| 5,674,254 A | 10/1997 | van Krieken |
| 5,683,431 A | 11/1997 | Wang |
| 5,683,434 A | 11/1997 | Archer |
| 5,697,953 A | 12/1997 | Kroll et al. |
| 5,697,956 A | 12/1997 | Bornzin |
| 5,704,365 A | 1/1998 | Albrecht et al. |
| 5,713,933 A | 2/1998 | Condie et al. |
| 5,715,812 A | 2/1998 | Deighan et al. |
| 5,718,720 A | 2/1998 | Prutchi et al. |
| 5,724,984 A | 3/1998 | Arnold et al. |
| 5,735,883 A | 4/1998 | Paul et al. |
| 5,738,102 A | 4/1998 | Lemelson |
| 5,779,645 A | 7/1998 | Olson et al. |
| 5,814,087 A | 9/1998 | Renirie |
| 5,817,027 A | 10/1998 | Arand et al. |
| 5,827,326 A | 10/1998 | Kroll et al. |
| 5,836,987 A | 11/1998 | Baumann et al. |
| 5,844,506 A | 12/1998 | Binstead et al. |
| 5,855,593 A | 1/1999 | Olson et al. |
| 5,857,977 A | 1/1999 | Caswell et al. |
| 5,860,918 A | 1/1999 | Schradi et al. |
| 5,861,011 A | 1/1999 | Stoop |
| 5,861,013 A | 1/1999 | Peck et al. |
| 5,871,512 A | 2/1999 | Hemming et al. |
| 5,873,898 A | 2/1999 | Hemming et al. |
| 5,876,353 A | 3/1999 | Riff et al. |
| 5,895,414 A | 4/1999 | Sanchez-Zambrano |
| 5,916,243 A | 6/1999 | Kenknight et al. |
| 5,944,680 A | 8/1999 | Christopherson et al. |
| 5,957,956 A | 9/1999 | Kroll et al. |
| 5,964,778 A | 10/1999 | Fugoso et al. |
| 5,974,340 A | 10/1999 | Kadhiresan |
| 5,987,352 A | 11/1999 | Klein et al. |
| 6,026,320 A | 2/2000 | Carlson et al. |
| 6,038,474 A | 3/2000 | Zhu et al. |
| 6,044,298 A | 3/2000 | Salo et al. |
| 6,045,513 A | 4/2000 | Stone et al. |
| 6,049,730 A | 4/2000 | Kristbjarnarson |
| 6,052,620 A | 4/2000 | Gillberg et al. |
| 6,055,454 A | 4/2000 | Heemels |
| 6,064,910 A | 5/2000 | Andersson et al. |
| 6,076,014 A | 6/2000 | Alt |
| 6,076,015 A | 6/2000 | Hartley et al. |
| 6,084,253 A | 7/2000 | Turner |
| 6,091,973 A | 7/2000 | Colla et al. |
| 6,101,416 A | 8/2000 | Sloman |
| 6,115,628 A | 9/2000 | Stadler et al. |
| 6,120,441 A | 9/2000 | Griebel et al. |
| 6,126,611 A | 10/2000 | Bourgeois et al. |
| 6,128,534 A | 10/2000 | Park et al. |
| 6,128,535 A | 10/2000 | Maarse |
| 6,132,384 A | 10/2000 | Christopherson et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | KenKnight |
| 6,148,234 A | 11/2000 | Struble |

(56) References Cited

U.S. PATENT DOCUMENTS

| | | |
|---|---|---|
| 6,163,724 A | 12/2000 | Hemming et al. |
| 6,166,554 A | 12/2000 | Webster et al. |
| 6,169,921 B1 | 1/2001 | KenKnight et al. |
| 6,175,766 B1 | 1/2001 | Bornzin et al. |
| 6,190,326 B1 | 2/2001 | McKinnon et al. |
| 6,192,275 B1 | 2/2001 | Zhu et al. |
| 6,221,011 B1 | 4/2001 | Bardy |
| 6,226,551 B1 | 5/2001 | Zhu et al. |
| 6,227,072 B1 | 5/2001 | Ritchey |
| 6,238,419 B1 | 5/2001 | Lindgren et al. |
| 6,251,126 B1 | 6/2001 | Ottenhoff et al. |
| 6,253,102 B1 | 6/2001 | Hsu et al. |
| 6,258,039 B1 | 7/2001 | Okamoto et al. |
| 6,259,947 B1 | 7/2001 | Olson et al. |
| 6,266,554 B1 | 7/2001 | Hsu et al. |
| 6,270,457 B1 | 8/2001 | Bardy |
| 6,272,377 B1 | 8/2001 | Sweeney et al. |
| 6,275,731 B1 | 8/2001 | Zhu et al. |
| 6,277,072 B1 | 8/2001 | Bardy |
| 6,280,380 B1 | 8/2001 | Bardy |
| 6,280,462 B1 | 8/2001 | Hauser et al. |
| 6,282,440 B1 | 8/2001 | Brodnick et al. |
| 6,285,907 B1 | 9/2001 | Kramer et al. |
| 6,299,581 B1 | 10/2001 | Rapoport et al. |
| 6,312,378 B1 | 11/2001 | Bardy |
| 6,312,388 B1 | 11/2001 | Marcovecchio et al. |
| 6,324,421 B1 | 11/2001 | Stadler et al. |
| 6,324,427 B1 | 11/2001 | Florio |
| 6,336,903 B1 | 1/2002 | Bardy |
| 6,345,201 B1 | 2/2002 | Sloman et al. |
| 6,351,669 B1 | 2/2002 | Hartley et al. |
| 6,351,673 B1 | 2/2002 | Ding et al. |
| 6,353,759 B1 | 3/2002 | Hartley et al. |
| 6,358,203 B2 | 3/2002 | Bardy |
| 6,360,127 B1 | 3/2002 | Ding et al. |
| 6,363,270 B1 | 3/2002 | Colla et al. |
| 6,363,281 B1 | 3/2002 | Zhu et al. |
| 6,368,284 B1 | 4/2002 | Bardy |
| 6,368,287 B1 | 4/2002 | Hadas |
| 6,371,922 B1 | 4/2002 | Baumann |
| 6,375,621 B1 | 4/2002 | Sullivan |
| 6,393,316 B1 | 5/2002 | Gillberg et al. |
| 6,398,728 B1 | 6/2002 | Bardy |
| 6,409,675 B1 | 6/2002 | Turcott |
| 6,411,848 B2 | 6/2002 | Kramer et al. |
| 6,415,174 B1 | 7/2002 | Bebehani et al. |
| 6,415,183 B1 | 7/2002 | Scheiner |
| 6,418,340 B1 | 7/2002 | Conley et al. |
| 6,418,343 B1 | 7/2002 | Zhang et al. |
| 6,421,564 B1 | 7/2002 | Yerich et al. |
| 6,424,234 B1 | 7/2002 | Stevenson |
| 6,424,865 B1 | 7/2002 | Ding |
| 6,434,417 B1 | 8/2002 | Lovett |
| 6,434,428 B1 | 8/2002 | Sloman et al. |
| 6,438,409 B1 | 8/2002 | Malik et al. |
| 6,438,410 B2 | 8/2002 | Hsu |
| 6,440,066 B1 | 8/2002 | Bardy |
| 6,449,503 B1 | 9/2002 | Hsu |
| 6,456,481 B1 | 9/2002 | Stevenson |
| 6,456,880 B1 | 9/2002 | Park et al. |
| 6,456,881 B1 | 9/2002 | Bornzin et al. |
| 6,459,929 B1 | 10/2002 | Hopper et al. |
| 6,463,327 B1 | 10/2002 | Lurie et al. |
| 6,466,820 B1 | 10/2002 | Juran et al. |
| 6,477,415 B1 | 11/2002 | Yerich et al. |
| 6,477,422 B1 | 11/2002 | Splett |
| 6,480,733 B1 | 11/2002 | Turcott |
| 6,480,734 B1 | 11/2002 | Zhang et al. |
| 6,487,443 B2 | 11/2002 | Olson et al. |
| 6,491,639 B1 | 12/2002 | Turcott |
| 6,493,586 B1 | 12/2002 | Stahmann et al. |
| 6,496,715 B1 | 12/2002 | Lee et al. |
| 6,505,067 B1 | 1/2003 | Lee et al. |
| 6,505,071 B1 | 1/2003 | Zhu et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,542,775 B2 | 4/2003 | Ding et al. |
| 6,553,259 B2 | 4/2003 | Mouchawar et al. |
| 6,564,106 B2 | 5/2003 | Guck et al. |
| 6,567,701 B2 | 5/2003 | Vonk |
| 6,574,507 B1 | 6/2003 | Bonnet |
| 6,587,726 B2 | 7/2003 | Lurie et al. |
| 6,589,188 B1 | 7/2003 | Street et al. |
| 6,595,927 B2 | 7/2003 | Pitts-Crick et al. |
| 6,597,951 B2 | 7/2003 | Kramer et al. |
| 6,600,949 B1 | 7/2003 | Turcott |
| 6,607,509 B2 | 8/2003 | Bobroff et al. |
| 6,611,712 B2 | 8/2003 | Spinelli et al. |
| 6,615,082 B1 | 9/2003 | Mandell |
| 6,615,083 B2 | 9/2003 | Küpper |
| 6,615,089 B1 | 9/2003 | Russie et al. |
| 6,618,619 B1 | 9/2003 | Florio et al. |
| 6,622,046 B2 | 9/2003 | Fraley et al. |
| 6,631,290 B1 | 10/2003 | Guck et al. |
| 6,640,136 B1 | 10/2003 | Helland et al. |
| 6,641,542 B2 | 11/2003 | Cho et al. |
| 6,654,637 B2 | 11/2003 | Rouw et al. |
| 6,658,293 B2 | 12/2003 | Vonk |
| 6,684,100 B1 | 1/2004 | Sweeney et al. |
| 6,690,967 B2 | 2/2004 | Meij et al. |
| 6,701,170 B2 | 3/2004 | Stetson |
| 6,708,058 B2 | 3/2004 | Kim et al. |
| 6,725,085 B2 | 4/2004 | Schwartzman et al. |
| 6,731,973 B2 | 5/2004 | Voith |
| 6,731,983 B2 | 5/2004 | Ericksen et al. |
| 6,731,984 B2 | 5/2004 | Cho et al. |
| 6,731,985 B2 | 5/2004 | Poore et al. |
| 6,738,668 B1 | 5/2004 | Mouchawar et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,772,008 B2 | 8/2004 | Zhu et al. |
| 6,773,404 B2 | 8/2004 | Poezevera et al. |
| 6,778,860 B2 | 8/2004 | Ostroff et al. |
| 6,782,291 B1 | 8/2004 | Bornzin et al. |
| 6,788,974 B2 | 9/2004 | Bardy et al. |
| 6,830,548 B2 | 12/2004 | Bonnet et al. |
| 6,834,204 B2 | 12/2004 | Ostroff et al. |
| 6,856,835 B2 | 2/2005 | Bardy et al. |
| 6,865,417 B2 | 3/2005 | Rissmann |
| 6,866,044 B2 | 3/2005 | Bardy et al. |
| 6,881,192 B1 | 4/2005 | Park |
| 6,884,218 B2 | 4/2005 | Olson |
| 6,885,893 B1 | 4/2005 | Lu |
| 6,888,538 B2 | 5/2005 | Ely et al. |
| 6,889,079 B2 | 5/2005 | Bocek et al. |
| 6,890,306 B2 | 5/2005 | Poezevera |
| 6,895,274 B2 | 5/2005 | Mower |
| 6,904,315 B2 | 6/2005 | Panken et al. |
| 6,904,320 B2 | 6/2005 | Park et al. |
| 6,915,160 B2 | 7/2005 | Auricchio et al. |
| 6,915,164 B2 | 7/2005 | Bradley et al. |
| 6,917,832 B2 | 7/2005 | Hutten et al. |
| 6,922,589 B2 | 7/2005 | Stahmann et al. |
| 6,925,324 B2 | 8/2005 | Shusterman |
| 6,925,330 B2 | 8/2005 | Kleine |
| 6,927,721 B2 | 8/2005 | Ostroff |
| 6,928,324 B2 | 8/2005 | Park et al. |
| 6,937,901 B2 | 8/2005 | Zhu et al. |
| 6,937,907 B2 | 8/2005 | Bardy et al. |
| 6,944,495 B2 | 9/2005 | MacAdam et al. |
| 6,944,579 B2 | 9/2005 | Shimizu |
| 6,950,702 B2 | 9/2005 | Sweeney |
| 6,950,705 B2 | 9/2005 | Bardy et al. |
| 6,952,608 B2 | 10/2005 | Ostroff |
| 6,952,610 B2 | 10/2005 | Ostroff |
| 6,954,670 B2 | 10/2005 | Ostroff |
| 6,959,214 B2 | 10/2005 | Pape et al. |
| 6,961,613 B2 | 11/2005 | Bjorling et al. |

(56) References Cited

U.S. PATENT DOCUMENTS

| | | |
|---|---|---|
| 6,961,619 B2 | 11/2005 | Casey |
| 6,973,350 B1 | 12/2005 | Levine et al. |
| 6,975,904 B1 | 12/2005 | Sloman |
| 6,978,178 B2 | 12/2005 | Sommer et al. |
| 6,983,264 B2 | 1/2006 | Shimizu |
| 6,988,003 B2 | 1/2006 | Bardy et al. |
| 6,993,379 B1 | 1/2006 | Kroll et al. |
| 6,993,389 B2 | 1/2006 | Ding et al. |
| 6,999,817 B2 | 2/2006 | Park et al. |
| 7,006,869 B2 | 2/2006 | Bradley |
| 7,025,730 B2 | 4/2006 | Cho et al. |
| 7,027,861 B2 | 4/2006 | Thompson |
| 7,027,868 B2 | 4/2006 | Rueter |
| 7,027,871 B2 | 4/2006 | Burnes et al. |
| 7,031,773 B1 | 4/2006 | Levine et al. |
| 7,039,459 B2 | 5/2006 | Bardy et al. |
| 7,039,465 B2 | 5/2006 | Bardy et al. |
| 7,043,299 B2 | 5/2006 | Erlinger et al. |
| 7,050,851 B2 | 5/2006 | Plombon et al. |
| 7,062,327 B2 | 6/2006 | Bradley |
| 7,065,400 B2 | 6/2006 | Schechter |
| 7,065,407 B2 | 6/2006 | Bardy et al. |
| 7,065,410 B2 | 6/2006 | Bardy et al. |
| 7,069,080 B2 | 6/2006 | Bardy et al. |
| 7,076,296 B2 | 7/2006 | Rissmann et al. |
| 7,079,988 B2 | 7/2006 | Albera et al. |
| 7,081,095 B2 | 7/2006 | Lynn et al. |
| 7,085,599 B2 | 8/2006 | Kim |
| 7,090,682 B2 | 8/2006 | Sanders et al. |
| 7,092,754 B2 | 8/2006 | Bardy et al. |
| 7,094,207 B1 | 8/2006 | Koh |
| 7,096,064 B2 | 8/2006 | Deno et al. |
| 7,103,404 B2 | 9/2006 | Stadler et al. |
| 7,107,093 B2 | 9/2006 | Burnes |
| 7,113,823 B2 | 9/2006 | Yonce et al. |
| 7,115,097 B2 | 10/2006 | Johnson |
| 7,117,036 B2 | 10/2006 | Florio |
| 7,120,495 B2 | 10/2006 | Bardy et al. |
| 7,123,960 B2 | 10/2006 | Ding et al. |
| 7,123,963 B2 | 10/2006 | Sawchuk et al. |
| 7,127,290 B2 | 10/2006 | Girouard et al. |
| 7,129,935 B2 | 10/2006 | Mackey |
| 7,139,610 B2 | 11/2006 | Ferek-Petric |
| 7,144,586 B2 | 12/2006 | Levy et al. |
| 7,146,212 B2 | 12/2006 | Bardy et al. |
| 7,149,575 B2 | 12/2006 | Ostroff et al. |
| 7,155,278 B2 | 12/2006 | King et al. |
| 7,160,252 B2 | 1/2007 | Cho et al. |
| 7,177,689 B2 | 2/2007 | Ternes et al. |
| 7,179,229 B1 | 2/2007 | Koh |
| 7,181,285 B2 | 2/2007 | Lindh et al. |
| 7,184,825 B2 | 2/2007 | Leinsing et al. |
| 7,184,835 B2 | 2/2007 | Kramer et al. |
| 7,191,003 B2 | 3/2007 | Greenhut et al. |
| 7,191,004 B2 | 3/2007 | Kim et al. |
| 7,194,302 B2 | 3/2007 | Bardy et al. |
| 7,194,309 B2 | 3/2007 | Ostroff et al. |
| 7,194,313 B2 | 3/2007 | Libbus |
| 7,203,540 B2 | 4/2007 | Ding et al. |
| 7,203,542 B2 | 4/2007 | Obel |
| 7,203,543 B2 | 4/2007 | Meyer et al. |
| 7,212,862 B2 | 5/2007 | Park et al |
| 7,218,925 B2 | 5/2007 | Crocker et al. |
| 7,225,016 B1 | 5/2007 | Koh |
| 7,225,021 B1 | 5/2007 | Park et al. |
| 7,225,035 B2 | 5/2007 | Brabec et al. |
| 7,228,173 B2 | 6/2007 | Cazares |
| 7,228,174 B2 | 6/2007 | Burnes et al. |
| 7,233,821 B2 | 6/2007 | Hettrick |
| 7,236,819 B2 | 6/2007 | Brockway et al. |
| 7,242,978 B2 | 7/2007 | Cao et al. |
| 7,242,983 B2 | 7/2007 | Frei et al. |
| 7,245,962 B2 | 7/2007 | Ciaccio et al. |
| 7,248,921 B2 | 7/2007 | Palreddy et al. |
| 7,248,925 B2 | 7/2007 | Bruhns et al. |
| 7,263,399 B2 | 8/2007 | Carlson |
| 7,277,754 B2 | 10/2007 | McCabe et al. |
| 7,277,757 B2 | 10/2007 | Casavant et al. |
| 7,286,876 B2 | 10/2007 | Yonce et al. |
| 7,299,086 B2 | 11/2007 | McCabe et al. |
| 7,299,093 B2 | 11/2007 | Zhu et al. |
| 7,308,311 B2 | 12/2007 | Sorensen et al. |
| 7,319,900 B2 | 1/2008 | Kim et al. |
| 7,330,761 B2 | 2/2008 | Zhang |
| 7,337,000 B2 | 2/2008 | Meyer et al. |
| 7,340,302 B1 | 3/2008 | Falkenberg et al. |
| 7,359,749 B2 | 4/2008 | Quenet et al. |
| 7,363,086 B1 | 4/2008 | Koh et al. |
| 7,369,889 B2 | 5/2008 | Aström et al. |
| 7,392,086 B2 | 6/2008 | Sathaye |
| 7,412,287 B2 | 8/2008 | Yonce et al. |
| 7,426,412 B1 | 9/2008 | Schecter |
| 7,438,686 B2 | 10/2008 | Cho et al. |
| 7,457,664 B2 | 11/2008 | Zhang et al. |
| 7,463,924 B2 | 12/2008 | Bardy et al. |
| 7,468,040 B2 | 12/2008 | Hartley et al. |
| 7,469,161 B1 | 12/2008 | Gandhi et al. |
| 7,471,983 B2 | 12/2008 | Voegele et al. |
| 7,477,932 B2 | 1/2009 | Lee et al. |
| 7,496,409 B2 | 2/2009 | Greenhut et al. |
| 7,499,751 B2 | 3/2009 | Meyer et al. |
| 7,509,170 B2 | 3/2009 | Zhang et al. |
| 7,519,423 B2 | 4/2009 | Begemann et al. |
| 7,555,336 B2 | 6/2009 | Sheth et al. |
| 7,555,340 B2 | 6/2009 | Dong et al. |
| 7,558,628 B2 | 7/2009 | Yonce et al. |
| 7,580,741 B2 | 8/2009 | Cazares et al. |
| 7,587,240 B2 | 9/2009 | Zhang et al. |
| 7,617,002 B2 | 11/2009 | Goetz |
| 7,620,452 B1 | 11/2009 | Russie |
| 7,647,108 B2 | 1/2010 | Freeberg |
| 7,653,431 B2 | 1/2010 | Cazares et al. |
| 7,657,314 B2 | 2/2010 | Sathaye et al. |
| 7,680,536 B2 | 3/2010 | Sathaye et al. |
| 7,684,861 B2 | 3/2010 | Sanders |
| 7,706,866 B2 | 4/2010 | Zhang et al. |
| 7,711,423 B2 | 5/2010 | Burnes et al. |
| 7,734,333 B2 | 6/2010 | Ghanem et al. |
| 7,734,347 B2 | 6/2010 | Sathaye et al. |
| 7,738,959 B2 | 6/2010 | Manrodt et al. |
| 7,761,162 B2 | 7/2010 | Dong et al. |
| 7,761,164 B2 | 7/2010 | Verhoef et al. |
| 7,765,004 B2 | 7/2010 | Stalsberg et al. |
| 7,792,585 B1 | 9/2010 | Shelchuk |
| 7,848,812 B2 | 12/2010 | Crowley et al. |
| 7,899,535 B2 | 3/2011 | Bohn et al. |
| 7,953,489 B2 | 5/2011 | Warren et al. |
| 7,957,803 B2 | 6/2011 | Zhang et al. |
| 7,996,072 B2 | 8/2011 | Haefner |
| 8,010,203 B2 | 8/2011 | DeMulling et al. |
| 8,036,743 B2 | 10/2011 | Savage et al. |
| 8,065,002 B2 | 11/2011 | Arand et al. |
| 8,078,276 B2 | 12/2011 | Dong et al. |
| 8,135,463 B2 | 3/2012 | Burnes et al. |
| 8,145,296 B2 | 3/2012 | Stalsberg et al. |
| 8,150,512 B2 | 4/2012 | Bornzin et al. |
| 8,160,700 B1 | 4/2012 | Ryu et al. |
| 8,175,703 B2 | 5/2012 | Dong et al. |
| 8,200,331 B2 | 6/2012 | Libbus et al. |
| 8,200,332 B2 | 6/2012 | Libbus et al. |
| 8,209,013 B2 | 6/2012 | Brooke et al. |
| 8,233,979 B1 | 7/2012 | Shelchuk |
| 8,265,736 B2 | 9/2012 | Sathaye et al. |
| 8,271,086 B2 | 9/2012 | Voegele et al. |
| 8,271,087 B2 | 9/2012 | Sathaye et al. |
| 8,306,622 B2 | 11/2012 | Arcot-Krishnamurthy et al. |
| 8,401,646 B2 | 3/2013 | Stadler et al. |
| 2002/0002327 A1 | 1/2002 | Grant et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0052631 A1 | 5/2002 | Sullivan et al. |
| 2002/0082658 A1 | 6/2002 | Heinrich et al. |

(56) References Cited

U.S. PATENT DOCUMENTS

| | | |
|---|---|---|
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2003/0023175 A1 | 1/2003 | Arzbaecher et al. |
| 2003/0065365 A1 | 4/2003 | Zhu |
| 2003/0083708 A1 | 5/2003 | Bradley et al. |
| 2003/0135248 A1 | 7/2003 | Stypulkowski |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0208241 A1 | 11/2003 | Bradley |
| 2003/0212436 A1 | 11/2003 | Brown |
| 2004/0064162 A1 | 4/2004 | Manrodt et al. |
| 2004/0082975 A1 | 4/2004 | Meyer et al. |
| 2004/0116978 A1 | 6/2004 | Bradley |
| 2004/0172065 A1 | 9/2004 | Sih et al. |
| 2004/0215253 A1 | 10/2004 | Weinberg |
| 2004/0215277 A1 | 10/2004 | Oosterhoff |
| 2004/0230229 A1 | 11/2004 | Lovett et al. |
| 2004/0260351 A1 | 12/2004 | Holmstrom |
| 2005/0004612 A1 | 1/2005 | Scholten et al. |
| 2005/0010120 A1 | 1/2005 | Jung et al. |
| 2005/0038478 A1 | 2/2005 | Klepfer |
| 2005/0043652 A1 | 2/2005 | Lovett et al. |
| 2005/0060002 A1 | 3/2005 | Zhu |
| 2005/0060007 A1 | 3/2005 | Goetz |
| 2005/0065587 A1 | 3/2005 | Gryzwa |
| 2005/0085865 A1 | 4/2005 | Tehrani |
| 2005/0113710 A1 | 5/2005 | Stahmann et al. |
| 2005/0131476 A1 | 6/2005 | Kim et al. |
| 2005/0131477 A1 | 6/2005 | Meyer et al. |
| 2005/0131478 A1 | 6/2005 | Kim et al. |
| 2006/0069322 A1 | 3/2006 | Zhang et al. |
| 2006/0074331 A1 | 4/2006 | Kim et al. |
| 2006/0074454 A1 | 4/2006 | Freeberg |
| 2006/0111747 A1 | 5/2006 | Cazares et al. |
| 2006/0116593 A1 | 6/2006 | Zhang et al. |
| 2006/0129193 A1 | 6/2006 | Zhang |
| 2006/0129194 A1 | 6/2006 | Zhang |
| 2006/0129195 A1 | 6/2006 | Sathaye |
| 2006/0129196 A1 | 6/2006 | Dong et al. |
| 2006/0129197 A1 | 6/2006 | Zhang et al. |
| 2006/0129198 A1 | 6/2006 | Zhang |
| 2006/0129199 A1 | 6/2006 | Zhang |
| 2006/0241711 A1 | 10/2006 | Sathaye |
| 2006/0247693 A1 | 11/2006 | Dong et al. |
| 2006/0247695 A1 | 11/2006 | Stalsberg et al. |
| 2006/0253043 A1 | 11/2006 | Zhang et al. |
| 2006/0253044 A1 | 11/2006 | Zhang et al. |
| 2007/0049974 A1 | 3/2007 | Li et al. |
| 2007/0055124 A1 | 3/2007 | Viswanathan |
| 2007/0129764 A1 | 6/2007 | Burnes |
| 2007/0142741 A1 | 6/2007 | Berthon-Jones et al. |
| 2007/0239057 A1 | 10/2007 | Pu et al. |
| 2007/0255321 A1 | 11/2007 | Gerber et al. |
| 2008/0004665 A1 | 1/2008 | McCabe et al. |
| 2008/0009909 A1 | 1/2008 | Sathaye et al. |
| 2008/0046019 A1 | 2/2008 | Sathaye |
| 2008/0071318 A1 | 3/2008 | Brooke et al. |
| 2008/0234556 A1 | 9/2008 | Brooke et al. |
| 2008/0294215 A1 | 11/2008 | Sathaye |
| 2008/0300644 A1 | 12/2008 | Sathaye |
| 2009/0030470 A1 | 1/2009 | Holmstrom |
| 2009/0043351 A1 | 2/2009 | Sathaye et al. |
| 2009/0043352 A1 | 2/2009 | Brooke et al. |
| 2009/0054946 A1 | 2/2009 | Sommer et al. |
| 2009/0210024 A1 | 8/2009 | Brooke |
| 2010/0125306 A1 | 5/2010 | McCabe et al. |
| 2010/0152801 A1 | 6/2010 | Koh et al. |
| 2010/0198292 A1 | 8/2010 | Honeck et al. |
| 2010/0305637 A1 | 12/2010 | McCabe et al. |
| 2010/0305638 A1 | 12/2010 | McCabe et al. |
| 2010/0305647 A1 | 12/2010 | McCabe et al. |
| 2010/0324617 A1 | 12/2010 | Ong |
| 2011/0004264 A1 | 1/2011 | Siejko et al. |
| 2011/0022110 A1 | 1/2011 | Min |
| 2011/0022112 A1 | 1/2011 | Min |
| 2011/0098770 A1 | 4/2011 | Ryu et al. |
| 2011/0098773 A1 | 4/2011 | Brisben et al. |
| 2011/0098774 A1 | 4/2011 | Brisben et al. |
| 2011/0152956 A1 | 6/2011 | Hincapie Ordonez et al. |
| 2011/0196441 A1 | 8/2011 | Ryu et al. |
| 2011/0196442 A1 | 8/2011 | Ryu et al. |
| 2011/0245890 A1 | 10/2011 | Brisben et al. |
| 2011/0319954 A1 | 12/2011 | Niazi et al. |
| 2012/0035685 A1 | 2/2012 | Saha et al. |
| 2012/0078320 A1 | 3/2012 | Schotzko et al. |
| 2012/0101543 A1 | 4/2012 | Demmer et al. |
| 2012/0101546 A1 | 4/2012 | Stadler et al. |
| 2012/0130442 A1 | 5/2012 | Rockweiler et al. |
| 2012/0150253 A1 | 6/2012 | Burnes et al. |
| 2012/0229496 A1 | 9/2012 | Bloemer |
| 2012/0271371 A1 | 10/2012 | Keel et al. |
| 2012/0290036 A1 | 11/2012 | Karamanoglu et al. |
| 2012/0296387 A1 | 11/2012 | Zhang et al. |
| 2012/0296388 A1 | 11/2012 | Zhang et al. |
| 2012/0323291 A1 | 12/2012 | Sathaye et al. |
| 2012/0330372 A1 | 12/2012 | Sathaye et al. |
| 2013/0006332 A1 | 1/2013 | Sommer et al. |
| 2013/0035737 A1 | 2/2013 | Ryu et al. |
| 2013/0035738 A1 | 2/2013 | Karst et al. |
| 2013/0046356 A1 | 2/2013 | Jensen et al. |
| 2013/0046369 A1 | 2/2013 | Eggen et al. |
| 2013/0053916 A1 | 2/2013 | Sambelashvili et al. |
| 2013/0053918 A1 | 2/2013 | Sambelashvili et al. |

FOREIGN PATENT DOCUMENTS

| | | |
|---|---|---|
| EP | 0940155 A2 | 9/1999 |
| EP | 1038498 A2 | 9/2000 |
| EP | 1151718 A2 | 11/2001 |
| EP | 1151718 A3 | 9/2002 |
| EP | 1038498 A3 | 1/2003 |
| EP | 1291038 A2 | 3/2003 |
| EP | 1291038 A3 | 1/2005 |
| EP | 1629863 A1 | 3/2006 |
| EP | 1151718 B1 | 1/2007 |
| EP | 1291038 B1 | 6/2007 |
| EP | 1629863 B1 | 6/2011 |
| EP | 1038498 B1 | 11/2011 |
| WO | 9904841 A1 | 2/1991 |
| WO | 9217240 A1 | 10/1992 |
| WO | 9220402 A1 | 11/1992 |
| WO | 0001438 A1 | 1/2000 |
| WO | 0017615 A2 | 3/2000 |
| WO | 0017615 A3 | 7/2000 |
| WO | 0240097 A1 | 5/2002 |
| WO | 0247761 A2 | 6/2002 |
| WO | 0247761 A3 | 6/2002 |
| WO | 02087696 A1 | 11/2002 |
| WO | 03003905 A2 | 1/2003 |
| WO | 03028550 A2 | 4/2003 |
| WO | 03028550 A3 | 5/2003 |
| WO | 03003905 A3 | 8/2003 |
| WO | 2004026398 A1 | 4/2004 |
| WO | 2004091720 A2 | 10/2004 |
| WO | 2005058412 A2 | 6/2005 |
| WO | 2005089865 A1 | 9/2005 |
| WO | 2006065707 A2 | 6/2006 |
| WO | 2007087025 A1 | 8/2007 |
| WO | 2006105474 A3 | 10/2007 |
| WO | 2008005270 A3 | 1/2008 |
| WO | 2009020639 A1 | 2/2009 |

OTHER PUBLICATIONS

Ajilore et al., "Nightcap: Laboratory and home-based evaluation of a portable sleep monitor," 32 Psychophysiology, 32-98, 1995. Abstract only.

Belouchrani et al., "Blind Source Separation Based on Time-Frequency Signal Representations," IEEE Transactions on Signal Processing, vol. 46, No. 11, pp. 2888-2897, Nov. 1998.

(56) References Cited

OTHER PUBLICATIONS

Cohen et al., "Capture Management Efficacy in children and young adults with endocardial and unipolar epicardial systems," Europace, vol. 6, pp. 248-255, 2004.

Comon, "Independent component analysis, A new concept?" Signal Processing, vol. 36, No. 3, pp. 287-314, Apr. 1994.

Gallois et al., "Multi-Channel Analysis of the EEG Signals and Statistic Particularities for Epileptic Seizure Forecast", Second Joint EMBS/BMES Conference, pp. 208-215, Oct. 23-26, 2002.

Gradaus et al., "Nonthoracotomy Implantable Cardioverter Defibrillator Placement in Children: Use of a Subcutaneous Array Leads and Abdominally Placed Implantable Cardioverter Defibrillators in Children", Journal of Cardiovascular Electrophysiology, vol. 12, No. 3, pp. 356-360, Mar. 2001.

Hartz et al., "New Approach to Defibrillator Insertion", Journal of Thoracic Cardiovascular Surgery, vol. 97, pp. 920-922, 1989.

Hyvärinen et al., "Independent Component Analysis: A Tutorial", Helsinki University of Technology, Apr. 1999.

Kolettis et al., "Submammary Implantation of a Cardioverter-Defibrillator with a Nonthoractomy Lead System", American Heart Journal, vol. 126, pp. 1222-1223, Nov. 1993.

Krahn et al., "Recurrent syncope. Experience with an implantable loop record", Cardiol. Clin., vol. 15(2), pp. 316-326, May 1997.

Leng et al., "Lead Configuration for Defibrillator Implantation in a Patient with Congenital Heart Disease and a Mechanical Prosthetic Tricuspid Valve", PACE, vol. 24, No. 8, pp. 1291-1292, Aug. 2001.

Park et al., "Use of an Implantable Cardioverter Defibrillator in an Eight-Month-Old Infant with Ventricular Fibrillation Arising from a Myocardial Fibroma", PACE, vol. 22, No. 1, pp. 138-139, Jan. 1999.

Rieta, et al., "Atrial Activity Extraction Based on Blind Source Separation as an Alternative to QRST Cancellation for Atrial Fibrillation Analysis", Computers in Cardiology, vol. 27, pp. 69-72, 2000.

Schuder et al., "Experimental Ventricular Defibrillation with an Automatic and Completely Implanted Syste", Trans. American Society Artif Int. Organs, vol. 16, pp. 207-212, 1970.

Schuder et al., "Transthoracic Ventricular Defibrillation in the Dog with Truncated and Untruncated Exponential Stimul"••, IEEE Transitions on Bio-Medical Engineering, vol. BME-18, No. 6, pp. 410-415, Nov. 1971.

Schuder et al., "Ventricular Defibrillation in the Dog Using Implanted and Partially Implanted Electrode Systems", American Journal of Cardiology, vol. 33, pp. 243-247, Feb. 1974.

Smits et al., "Defibrillation Threshold (DFT) Model of a Fully Subcutaneous ICD System, Europace Supplements", vol. 2, Jun. 2001 at col. 778, p. B83.

Splett et al. "Determination of Pacing Capture in Implantable Defibrillators: Benefit of Evoked Response Detection Using RV Coil to Can Vector," PACE, vol. 23, 2000, pp. 1645-1650.

Stirbis et al., "Optimizing of the Shape of Implanted Artificial Pacemakers", Kaunas Medical Institute, Translated from Meditsinskaya Tekhnika, No. 6, pp. 25-27, 1986.

Verrier et al., "Sleep, dreams, and sudden death: the case for sleep as an autonomic stress test for the heart", 31 Cardiovascular Research, 181-211, 1996.

Verrier et al., "Sleep Related Cardiovascular Risk: New Home-Based MonitoringTechnology for Improved Diagnosis and Therapy", 2 A.N.E. 158-175, 1997.

Waldemark et al., "Detection of Apnea using Short Window FFT Technique and Artificial Neural Network", 3390 SPIE International Society for Optical Engineering 122-133, 1998. Partial article.

Zarzoso et al., "Blind Separation of Independent Sources for Virtually Any Source Probability Density Function", IEEE Transactions on Signal Processing, vol. 47, No. 9, pp. 2419-2432, Sep. 1999.

Zarzoso et al., "Noninvasive Fetal Electrocardiogram Extraction: Blind Separation Versus Adaptive Noise Cancellation", IEEE Transactions on Biomedical Engineering, vol. 48, No. 1, pp. 12-18, Jan. 2001.

METHOD AND APPARATUS TO PERFORM ELECTRODE COMBINATION SELECTION

This application is a continuation of U.S. application Ser. No. 13/595,688, filed Aug. 27, 2012; which is a continuation of U.S. application Ser. No. 11/890,668, filed Aug. 7, 2007, now U.S. Pat. No. 8,265,736, the disclosures of which are hereby incorporated herein by reference in their entirety.

FIELD OF THE INVENTION

The present invention relates generally to cardiac devices and methods, and, more particularly, to selection of one or more electrode combinations from a plurality of electrodes.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sin θ-atrial (SA) node to be rapidly conducted throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management (CRM) devices have been developed that provide pacing stimulation to one or more heart chambers in an attempt to improve the rhythm and coordination of atrial and/or ventricular contractions. CRM devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver stimulation to the heart in accordance with various therapies for treating cardiac arrhythmias and dyssynchrony.

Pacemakers are CRM devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue, generating an evoked response that generates a propagating depolarization wave that results in a contraction of the heart chamber. It is desirable for a pace pulse to have sufficient energy to stimulate capture of the heart chamber without expending energy significantly in excess of the capture threshold. Pacing in excess of a capture threshold can cause excessive energy consumption, require premature battery replacement, and can unintentionally stimulate nerves or muscles. However, if a pace pulse energy is too low, the pace pulses may not reliably produce a contractile response in the heart chamber and may result in ineffective pacing that does not improve cardiac function or cardiac output.

Electrical cardiac therapies include other complexities. For example, low impedance between an anode and cathode pair can require excessive energy delivery, causing high energy consumption and prematurely depleting the battery resources. In another example, excessively high impedance between an anode and cathode pair indicates a problem with the stimulation circuit (i.e. lead damage), resulting in a lack of therapy.

Delivering electrical cardiac therapy may involve selection of an electrode combination to which the electrical cardiac therapy is delivered. Devices for cardiac pacing and sensing may utilize a number of electrodes electrically coupled to the heart at one or more pacing sites, the electrodes configured to sense and/or pace a heart chamber. Each different combination of electrodes between which energy can be delivered constitutes a vector. Pacing via multiple intra-chamber electrode pairs may be beneficial, for example, to stimulate the heart tissue in a coordinated sequence that improves contractile function of the heart chamber.

The present invention provides methods and systems for selecting an electrode combination and provides various advantages over the prior art.

SUMMARY OF THE INVENTION

The present invention involves approaches for selecting one or more electrode combinations. One embodiment of the invention is directed to a method for evaluating, for each electrode combination of a plurality of electrode combinations, one or more first parameters produced by electrical stimulation of the electrode combination, the first parameters supportive of cardiac function consistent with a prescribed therapy. In some embodiments of the present invention, a first parameter is a capture threshold.

The method for selecting an electrode combination can include evaluating, for each electrode combination of the plurality of electrode combinations, one or more second parameters produced by the electrical stimulation of the electrode combination, the second parameters not supportive of cardiac function consistent with a prescribed therapy. In some embodiments of the present invention, a second parameter is indicative of activation of extra-cardiac tissue.

The method for selecting an electrode combination can further include determining an order for at least some of the electrode combinations of the plurality of electrode combinations based on the evaluations of the first parameters and the second parameters. In some embodiments of the present invention, ordering electrode combinations can include ranking the electrode combinations.

The method for selecting an electrode combination can further include selecting one or more electrode combinations based on the order. Selection of the electrode combination may be done by a human or automatically by a processor executing program instructions stored in memory. The method can further include delivering an electrical stimulation therapy using the selected one or more electrode combinations. Any of these method steps can be performed automatically by a CRM system.

Another embodiment of the invention is directed to a CRM system for selecting an electrode combination. The CRM can include a plurality of cardiac electrodes electrically coupled respectively to a plurality of electrode combinations. The electrodes can further be physically coupled to an implantable housing.

According to one aspect of the present invention, the implantable housing can contain circuitry configured to evaluate, for each electrode combination of a plurality of electrode combinations, one or more first parameters produced by electrical stimulation of the electrode combination, the first parameters supportive of cardiac function consistent with a prescribed therapy and circuitry configured to evaluate, for each electrode combination of the plurality of electrode combinations, one or more second parameters produced by the electrical stimulation of the electrode combination, the second parameters not supportive of cardiac function consistent with a prescribed therapy.

The CRM system can further include an electrode combination processor configured to determine an order for at least some of the electrode combinations of the plurality of electrode combinations based on the evaluations of the first parameters and the second parameters. The electrode combination processor can be contained within the implantable housing, or may be contained in a patient-external housing.

The implantable housing may further include a therapy circuit configured to deliver electrical stimulation therapy using the electrode combinations.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
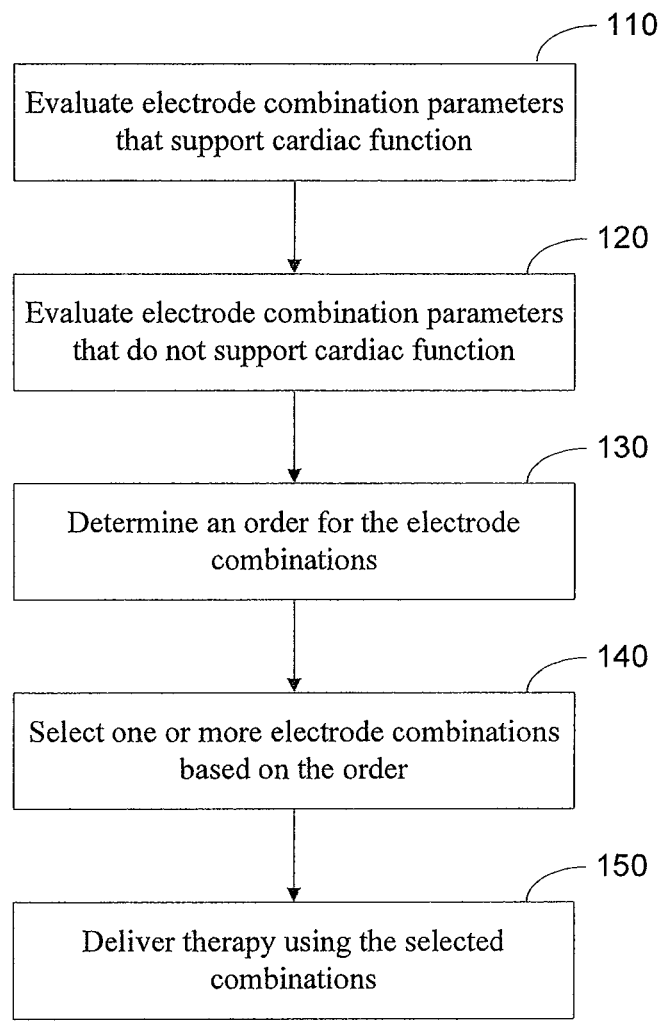
FIG. 1 is a flowchart illustrating a method of selecting an electrode combination in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such a device or system need not include all of the features described herein, but may be implemented to include selected features that provide for useful structures and/or functionality. Such a device or system may be implemented to provide a variety of therapeutic or diagnostic functions.

In multi-electrode pacing systems, multiple pacing electrodes may be disposed in a single heart chamber, in multiple heart chambers, and/or elsewhere in a patient's body. Electrodes used for delivery of pacing pulses may include one or more cathode electrodes and one or more anode electrodes. Pacing pulses are delivered via the cathode/anode electrode combinations, where the term "electrode combination" denotes that at least one cathode electrode and at least one anode electrode are used. An electrode combination may involve more than two electrodes, such as when multiple electrodes that are electrically connected are used as the anode and/or multiple electrodes that are electrically connected are used as the cathode. Typically, pacing energy is delivered to the heart tissue via the cathode electrode(s) at one or more pacing sites, with a return path provided via the anode electrode(s). If capture occurs, the energy injected at the cathode electrode site creates a propagating wavefront of depolarization which may combine with other depolarization wavefronts to trigger a contraction of the cardiac muscle. The cathode and anode electrode combination that delivers the pacing energy defines the pacing vector used for pacing. The position of the cathode relative to cardiac tissue can be used to define an electrode combination and/or a pacing site.

Pacing pulses may be applied through multiple electrodes (i.e., pacing vectors defined by various electrode combinations) in a single cardiac chamber in a timed sequence during the cardiac cycle to improve contractility and enhance the pumping action of the heart chamber. It is desirable for each pacing pulse delivered via the multiple electrode combinations to capture the cardiac tissue proximate the cathode electrode. The pacing energy required to capture the heart is dependent on the electrode combination used for pacing, and different electrode combinations can have different energy requirements for capture. Particularly in the left ventricle, the minimum energy required for capture, denoted the capture threshold, may be highly dependent on the particular electrode combination used.

Pacing characteristics of therapy delivery using each electrode combination of a plurality of possible electrode combinations are dependent on many factors, including the distance between the electrodes, proximity to target tissue, type of tissue contacting and between the electrodes, impedance between the electrodes, resistance between the electrodes, and electrode type, among other factors. Such factors can influence the capture threshold for the electrode combination, among other parameters. Pacing characteristics can vary with physiologic changes, electrode migration, physical activity level, body fluid chemistry, hydration, and disease state, among others. Therefore, the pacing characteristics for each electrode combination are unique, and some electrode combinations may work better than others for delivering a particular therapy that improves cardiac function consistent with a prescribed therapy.

In this way, electrode combination selection should take into consideration at least the efficacy of one or more electrode combinations of a plurality of electrodes in supporting cardiac function in accordance with a prescribed therapy. The efficacy of one or more electrode combinations of a plurality of electrodes in supporting cardiac function in accordance with a prescribed therapy can be evaluated by consideration of one or more parameters produced by electrical stimulation, such as capture threshold.

Electrical stimulation delivered to one body structure to produce a desired therapeutic activation may undesirably cause activation of another body structure. For example, electrical cardiac pacing therapy can inadvertently stimulate bodily tissue, including nerves and muscles. Stimulation of extra-cardiac tissue, including phrenic nerves, the diaphragm, and skeletal muscles, can cause patient discomfort and interfere with bodily function.

A patient's evoked response from an electrical cardiac therapy can be unpredictable between electrode combinations. For example, an electrical cardiac therapy delivered using one electrode combination may produce an undesirable activation while an identical electrical cardiac therapy delivered using another electrode combination may not produce the undesirable activation. As such, selecting an appropriate electrode combination, such as one electrode combination of a plurality of electrode combinations made possible by a multi-electrode lead that affects the desired cardiac response with the least amount of energy consumption and that does not unintentionally stimulate tissue, can be many-factored and complicated.

Manually testing each parameter of interest for each possible cathode-anode electrode combination can be a time consuming process for doctors, clinicians, and programmers. Furthermore, it can be difficult to sort through numerous different parameters for multiple pacing electrode combinations and understand the various tissue activation responses of electrical therapy delivered using various electrode combinations. Systems and methods of the present invention can simplify these and other process.

Devices of the present invention may facilitate selection of one or more electrode combinations using various parameters of interest. A device may be preset for parameters of interest and/or a physician may select beneficial parameters of interest and/or non-beneficial parameters of interest. The parameters that are of interest can vary between patients, depending on the patient's pathology. Beneficial parameters are parameters which are associated with supported cardiac function in accordance with a prescribed therapy and/or are the intended result of a prescribed therapy. Non-beneficial parameters are parameters which are not associated with supported cardiac function in accordance with a prescribed therapy and/or are not the intended result of a prescribed therapy.

The flowchart of FIG. 1 illustrates a process for selecting one or more electrode combinations and delivering a therapy using the one or more selected electrode combinations. Although this method selects an electrode combination and delivers a therapy using the electrode combination, not all embodiments of the current invention perform all of the steps 110-150.

Parameters that support cardiac function are evaluated 110 for a plurality of electrode combinations.

A parameter that supports cardiac function is any parameter that is indicative of a physiological effect consistent with one or more therapies prescribed for the patient. For example, successful capture of a heart chamber can be indicative of cardiac contractions that are capable of pumping blood, where ventricular pacing was a prescribed therapy for the patient. Parameters that support cardiac function consistent with a prescribed therapy can be beneficial parameters, as they can be indicative of intended therapy effects (e.g., capture).

In some embodiments of the current invention, evaluating a parameter that supports cardiac function includes detecting whether electrical therapy delivered through each electrode combination of a plurality of electrode combinations improves the patient's cardiac function, consistent with a prescribed therapy, relative to cardiac function without the electrical therapy delivered using the respective electrode combination.

Parameters that do not support cardiac function are evaluated 120 for at least some of the plurality of electrode combinations. A parameter that does not support cardiac function is any parameter that produces a physiological effect inconsistent with the patient's prescribed therapy.

In some embodiments of the present invention, parameters that do not support cardiac function include parameters that are indicative of undesirable stimulation, the undesirable stimulation not consistent with a therapy prescribed for the patient. For example, delivering an electrical cardiac therapy using a particular electrode combination may unintentionally stimulate skeletal muscles, causing discomfort to the patient, not improving cardiac function consistent with a prescribed therapy, and possibly interfering with improving cardiac function and/or delivery of the prescribed therapy. Parameters that do not support cardiac function consistent with a prescribed therapy can be non-beneficial parameters, as they can be indicative of unintended effects of the therapy.

The electrode combinations can be ordered 130. The order can be based on the evaluations 120 and 130 of the parameters that support cardiac function and the parameters that do not support cardiac function. Ordering may be establishing or recognizing relationships between various electrode combinations based on parameters.

Ordering can be performed manually or automatically. For example, a clinician can consider the parameters that support cardiac function and the parameters that do not support cardiac function and order the electrode combinations based on the parameters. Ordering can also be performed algorithmically by a processor executing instructions stored in memory, the processor ordering the electrode combinations based on parameter information stored in memory. For example, a data processor may algorithmically order a plurality of electrode combinations based on parameter information stored in memory, giving priority in the order to electrode combinations that can best implement the prescribed therapy while minimizing the occurrence of undesirable events inconsistent with the prescribed therapy.

One or more electrode combinations can be selected 140 based on the order of the electrode combinations. Selection of one or more electrode combinations may be done manually by a clinician reviewing the electrode combination order and inputting a selection into the device. Selection may also be done automatically, such as by a processor executing instructions stored in memory, the processor algorithmically selecting the electrode combination based on electrode combination order information stored in memory.

After electrode combination selection, therapy can be delivered 150 using the one or more selected electrode combinations. The various steps of FIG. 1, as well as the other steps disclosed herein, can be performed automatically, such that no direct human assistance is needed to initiate or perform the various discrete steps.

Figure 2:
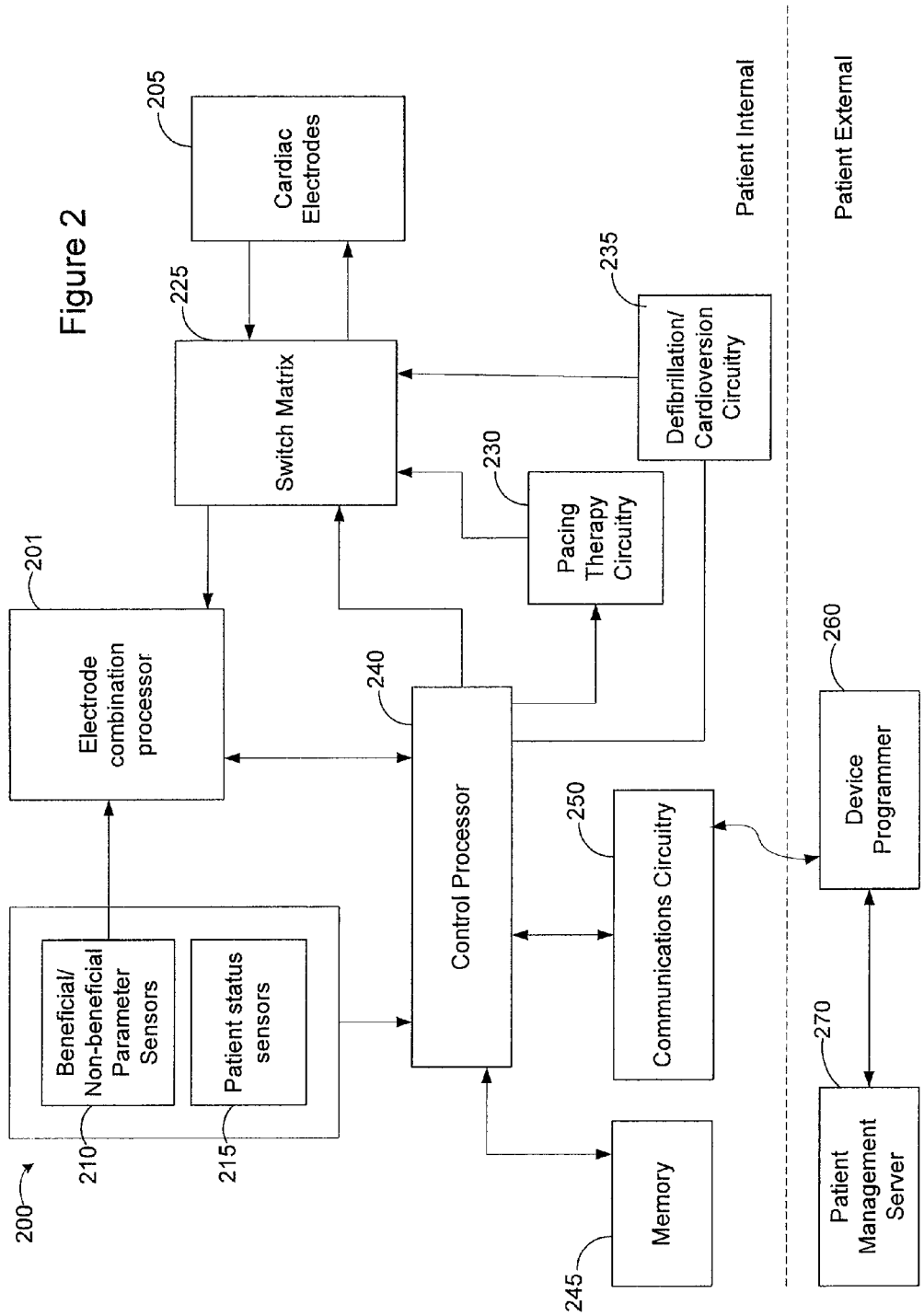
FIG. 2 is a block diagram of a system incorporating electrode combination selection circuitry in accordance with embodiments of the invention.

FIG. 2 is a block diagram of a CRM device 200 that may incorporate circuitry for selecting an electrode combination in accordance with embodiments of the present invention. The CRM device 200 includes pacing therapy circuitry 230 that delivers pacing pulses to a heart. The CRM device 200 may optionally include defibrillation cardioversion circuitry 235 configured to deliver high energy defibrillation or cardioversion stimulation to the heart for terminating dangerous tachyarrhythmias.

The pacing pulses are delivered via multiple cardiac electrodes 205 (electrode combinations) disposed at multiple locations within a heart, wherein a location can correspond to a pacing site. Certain combinations of the electrodes 205 may be designated as alternate electrode combinations while other combinations of electrodes 205 are designated as initial electrode combinations. Two or more electrodes may be disposed within a single heart chamber. The electrodes 205 are coupled to switch matrix 225 circuitry used to selectively couple electrodes 205 of various pacing configurations to electrode combination processor 201 and/or other components of the CRM device 200. The electrode combination processor 201 is configured to receive information gathered via the cardiac electrodes 205 and beneficial/non-beneficial parameter sensors 210. The electrode combination processor 201 can perform various functions, including evaluating electrode combination parameters that support cardiac function, evaluating electrode combination parameters that do not support cardiac function, determining an order for the electrode combinations, and selecting one or more electrode combinations based on the order, as well as other processes.

The control processor 240 can use patient status information received from patient status sensors 215 to schedule or initiate any of the functions disclosed herein, including selecting an electrode combination. Patient status sensors 215 may include an activity monitor, a posture monitor, a respiration monitor, an oxygen level monitor, and an accelerometer, among others.

A CRM device 200 typically includes a battery power supply (not shown) and communications circuitry 250 for communicating with an external device programmer 260 or other patient-external device. Information, such as data, parameter measurements, parameter evaluations, parameter estimates, electrode combination orders, electrode combination selections, and/or program instructions, and the like, can be transferred between the device programmer 260 and patient management server 270, CRM device 200 and the device programmer 260, and/or between the CRM device 200 and the patient management server 270 and/or other external system. In some embodiments, the electrode combination processor 201 may be a component of the device programmer 260, patient management server 270, or other patient external system.

The CRM device 200 also includes a memory 245 for storing program instructions and/or data, accessed by and through the control processor 240. In various configurations, the memory 245 may be used to store information related to activation thresholds, parameters, orders, measured values, program instructions, and the like.

Parameters can be measured by Beneficial/Non-Beneficial Parameter Sensors 210. Parameter Sensors 210 can include the various sensors discussed herein or known in the art, including accelerometers, acoustic sensors, electrical signal sensors, pressure sensors, and the like.

Figure 3:
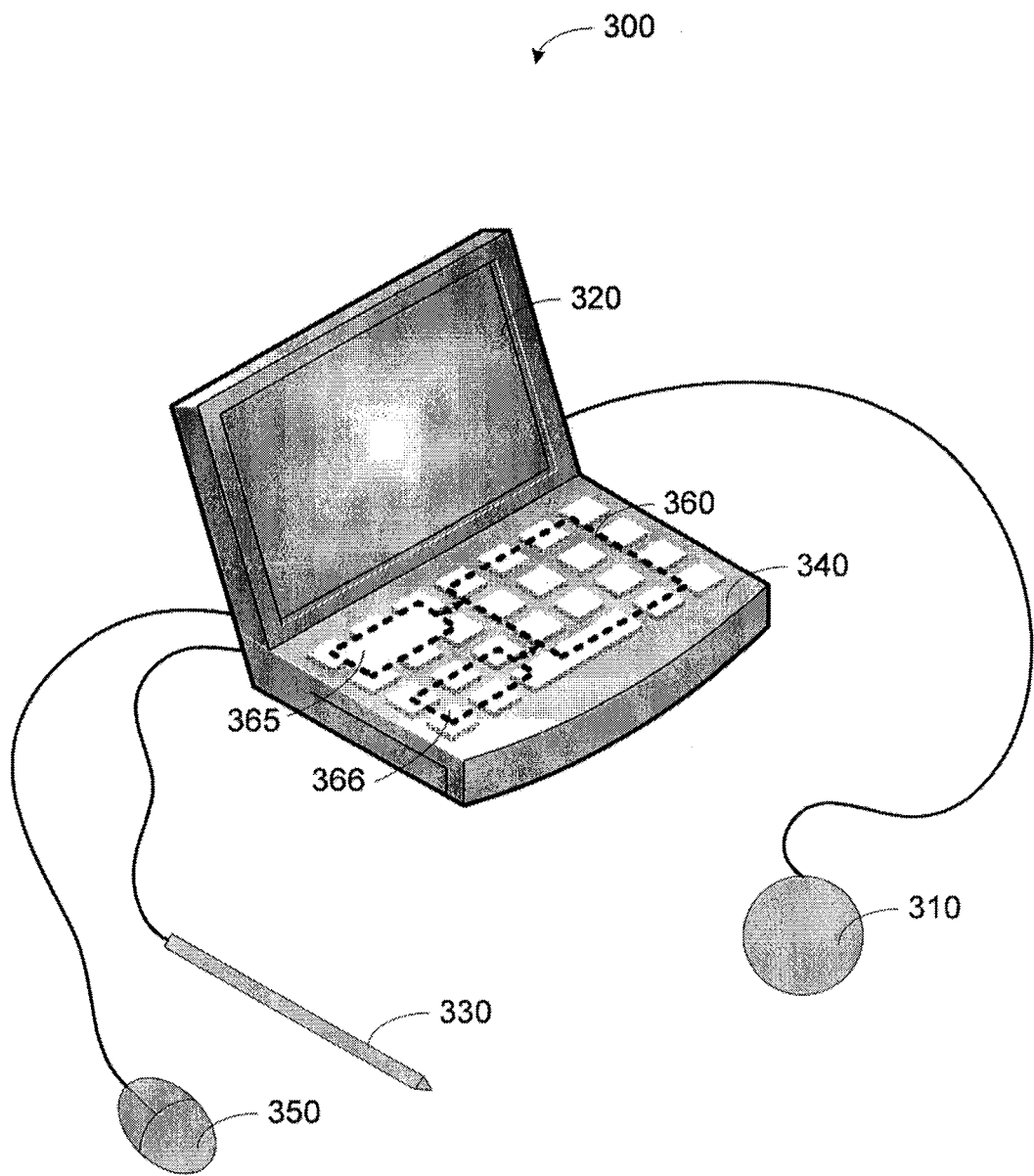
FIG. 3 is a diagram illustrating a patient-external device that provides a user interface allowing a human analyst to interact with information and program an implantable medical device in accordance with embodiments of the invention.

FIG. 3 illustrates a patient external device 300 that provides a user interface configured to allow a human analyst, such as a physician, or patient, to interact with an implanted medical device. The patient external device 300 is described as a CRM programmer, although the methods of the invention are operable on other types of devices as well, such as portable telephonic devices, computers or patient information servers used in conjunction with a remote system, for example. The programmer 300 includes a programming head 310 which is placed over a patient's body near the implant site of an implanted device to establish a telemetry link between a CRM and the programmer 300. The telemetry link allows the data collected by the implantable device to be downloaded to the programmer 300. The downloaded data is stored in the programmer memory 365.

The programmer 300 includes a graphics display screen 320, e.g., LCD display screen, that is capable of displaying graphics, alphanumeric symbols, and/or other information. For example, the programmer 300 may graphically display one or more of the parameters downloaded from the CRM on the screen 320. The display screen 320 may include touch-sensitive capability so that the user can input information or commands by touching the display screen 320 with a stylus 330 or the user's finger. Alternatively, or additionally, the user may input information or commands via a keyboard 340 or mouse 350.

The programmer 300 includes a data processor 360 including software and/or hardware for performing the methods disclosed here, using program instructions stored in the memory 365 of the programmer 300. In one implementation, sensed data is received from a CRM via communications circuitry 366 of the programmer 300 and stored in memory 365. The data processor 360 evaluates the sensed data, which can include information related to beneficial and non-beneficial parameters. The data processor 360 can also perform other method steps discussed herein, including comparing parameters and ordering the electrode combinations, among others. Parameter information, electrode combination information, and an electrode combination order, as well as other information, may be presented to a user via a display screen 320. The parameters used for ordering the electrode combinations may be identified by the user or may be identified by the data processor 360, for example.

In some embodiments of the current invention, ordering the electrode combinations may be determined by a user and entered via the keyboard 320, the mouse 350, or stylus 330 for touch sensitive display applications. In some embodiments of the current invention, the data processor 360 executes program instructions stored in memory to order a plurality of electrode combinations based on sensed beneficial and non-beneficial parameters. The electrode combination order determined by the data processor 360 is then displayed on the display screen, where a human analyst then reviews the order and selects one or more electrode combinations for delivering an electrical cardiac therapy.

Figure 4:
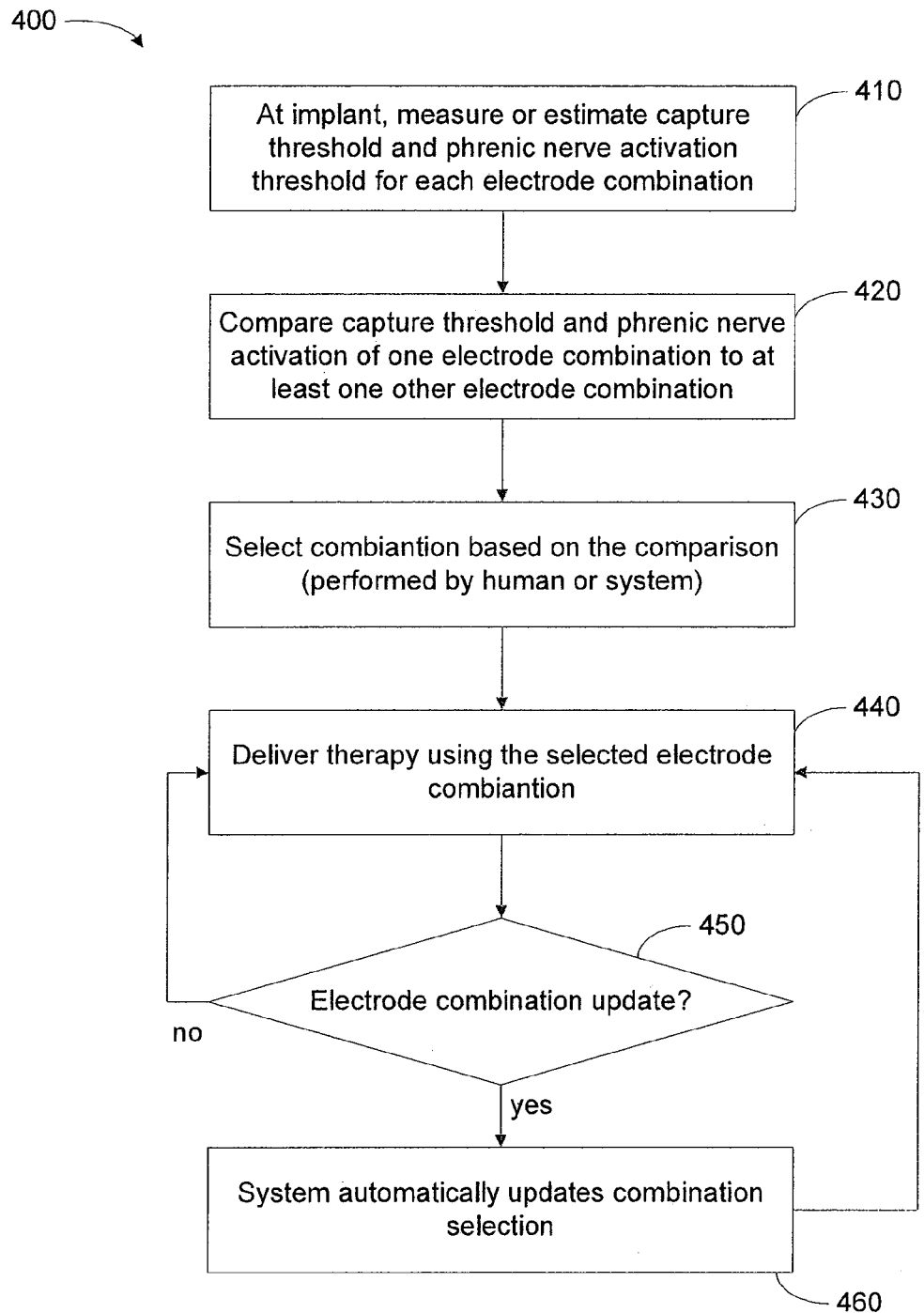
FIG. 4 is a flowchart illustrating a method of selecting one or more electrode combinations based on capture threshold and phrenic nerve activation parameters and automatically updating the electrode combination selection in accordance with embodiments of the invention.

The flowchart of FIG. 4 illustrates a process 400 for selecting one or more electrode combinations based on capture threshold and phrenic nerve activation parameters and automatically updating the electrode combination selection. The process 400 includes measuring or estimating 410 a capture threshold and phrenic nerve activation threshold for each electrode combination at implant. The capture threshold for a particular electrode combination may be determined by a capture threshold test. For example, the capture threshold test may step down the pacing energy for successive pacing cycles until loss of capture is detected.

The process 400 of FIG. 4 includes measuring or estimating 410 a phrenic nerve activation threshold for each electrode combination. The phrenic nerve innervates the diaphragm, so stimulation of the phrenic nerve can cause a patient to experience a hiccup. Electrical stimulation that causes a hiccup can be uncomfortable for the patient, and can interfere with breathing. Additionally, phrenic nerve stimulation and/or diaphragmatic stimulation that is inconsistent with the patient's therapy and/or does not support cardiac function is undesirable and can interfere with the intended therapy.

Phrenic nerve activation, and/or a phrenic nerve activation threshold, may be measured for an electrode combination by delivering electrical energy across the electrode combination and sensing for phrenic nerve activation. The energy delivered could also be used to simultaneously perform other tests, such as searching for a capture threshold. If no phrenic nerve activation is sensed using the level of electrical energy delivered, the energy level can be iteratively increased for subsequent trials of delivering electrical energy and monitoring for phrenic nerve activation until phrenic nerve activation is sensed. The electrical energy level at which phrenic nerve activation is detected can be the phrenic nerve activation threshold. Alternatively, the level of electrical energy may be decreased or otherwise adjusted until phrenic nerve activation is not detected.

Methods for evaluating phrenic nerve activation are disclosed in U.S. Pat. Nos. 6,772,008 and 7,392,086, which are herein incorporated by reference in their respective entireties.

The process 400 of FIG. 4 further includes comparing 420 the capture threshold and phrenic nerve activation threshold of one electrode combination to at least one other electrode combination. Comparing can be performed in various ways, including by a human, such as a doctor or programmer, or automatically by a processor executing instructions stored in memory. In some embodiments of the present invention, some aspects of comparing 420 can be done by a human while some aspects of comparing 420 can be done electronically.

Comparing 420 can include comparing the capture thresholds of the electrode combinations to one another. Such a comparison can identify which electrode combinations are associated with the lowest capture thresholds. Comparing 420 can also include comparing the occurrence, amounts, and/or thresholds of phrenic nerve activation of the electrode combinations to one another. Such a comparison can identify which electrode combinations are associated with the highest and/or lowest occurrence, amount and/or threshold of phrenic nerve stimulation. Other parameters discussed herein can also be similarly compared in this and other embodiments of the present invention.

Comparing 420 can be multidimensional, such that multiple metrics are compared for multiple electrode combinations. For example, comparing 420 may consider capture threshold and phrenic nerve activation for multiple electrode combinations to indicate which electrode combination has the lowest relative capture threshold and the least relative phrenic nerve activation.

The process 400 of FIG. 4 further includes selecting 430 an electrode combination based on the comparison of step 420. Selecting 430 may be done entirely by a human, entirely by a system algorithmically, or partially by a human and partially by the system.

Selecting 430 can be done according to criteria. For example, the results of the comparison can be reviewed and the electrode combination(s) matching a predetermined criterion can be selected. The criteria may be predefined by a human. Different sets of criteria may be created by a human, stored in memory, and then selected by a doctor or programmer for use, such as use in selecting 430 an electrode combination based on the comparison.

By way of example, selecting 430 can include selecting according to the criteria that the selected electrode combination be the combination with the lowest capture threshold that was not associated with phrenic nerve activation. Other criteria that can be used additionally or alternatively include responsiveness to CRT, low energy consumption, extra-cardiac activation, dP/dt, among others indicative of beneficial parameters consistent with a prescribed therapy or non-beneficial parameters inconsistent with the prescribed therapy. The electrode combination fitting such criteria can be identified for selection based on the comparison 430.

The process 400 of FIG. 4 further includes delivering 440 therapy using the selected electrode combination. Delivering 440 therapy can include any therapy delivery methods disclosed herein or known in the art.

The process 400 of FIG. 4 further includes determining whether an electrode combination update is indicated 450. An electrode combination update may be indicated in various ways, including detecting a condition necessitating an electrode combination update (such as loss of capture, change in posture, change in disease state, detection of non-therapeutic activation, and/or short or long term change in patient activity state, for example). An electrode combination update may be initiated according to a predetermined schedule, or an indication given by a human or system.

In the particular embodiment of FIG. 4, if it is determined that an electrode combination update is indicated 450, then the system automatically updates 460 the electrode combination selection 460. In various embodiments of the current invention, automatically updating 460 electrode combination selection can include some or all of the various methods of the process 400 or can be based on other methods. According to various embodiments of the present invention, therapy can then be delivered 440 using the updated electrode combination. The updated electrode combination can be different from the electrode combination previously used to deliver therapy, or the updated electrode combination can be the same electrode combination, despite the update.

Although the embodiment of FIG. 4 exemplified aspects of the present invention using capture threshold as a parameter that supports cardiac function consistent with a prescribed therapy, numerous other parameters can alternatively, or additionally, be used to indicate cardiac function.

For example, a parameter that supports cardiac function can include a degree of responsiveness to cardiac resynchronization therapy (CRT). As one of ordinary skill in the art would understand, when attempting CRT, it is preferable to select an electrode combination with a higher degree of responsiveness to CRT relative to other electrode combinations. Responsiveness to CRT, including methods to detect responsiveness, is disclosed in U.S. Patent Publication No. 2008/0177344, which is hereby incorporated by reference in its entirety.

Parameters that support cardiac function consistent with a prescribed therapy may be related to contractility, blood pressure, dP/dt, stroke volume, cardiac output, contraction duration, hemodynamics, ventricular synchronization, activation sequence, depolarization and/or repolarization wave characteristics, intervals, responsiveness to cardiac resynchronization, electrode combination activation timing, stimulation strength/duration relationship, and battery consumption.

Various parameters that may be used for electrode combination selection are discussed in U.S. Patent Publication Nos. 2010/0023078 and 2008/0004667, both of which are hereby incorporated herein by reference in each respective entirety. Each of these incorporated references include parameters that support cardiac function and parameters that do not support cardiac function, the parameters usable in the methods disclosed herein for selecting an electrode combination.

Although the embodiment of FIG. 4 exemplified aspects of the present invention using phrenic nerve activation as a parameter that does not support cardiac function consistent with a prescribed therapy, numerous other parameters can alternatively, or additionally, be used. Parameters that do not support cardiac stimulation consistent with a prescribed therapy can include, but are not limited to, extra-cardiac stimulation, non-cardiac muscle stimulation (ex. skeletal muscle stimulation), unintended nerve stimulation, anodal cardiac stimulation, and excessively high or low impedance.

For example, a parameter that does not support cardiac function consistent with a prescribed therapy can include skeletal muscle activation, undesirable modes of cardiac activation, and/or undesirable nerve activation. Commonly owned U.S. Pat. No. 6,772,008, which is incorporated herein by reference, describes methods and systems that may be used in relation to detecting undesirable tissue activation. Skeletal muscle activation may be detected, for example, through the use of an accelerometer and/or other circuitry that senses accelerations indicating muscle movements that coincide with the output of the stimulation pulse.

Other methods of measuring tissue activation may involve, for example, the use of an electromyogram sensor (EMG), microphone, and/or other sensors. In one implementation, activation of the laryngeal muscles may be automatically detected using a microphone to detect the patient's coughing response to undesirable activation of the laryngeal muscles or nerves due to electrical stimulation.

Undesirable nerve or muscle activation may be detected by sensing a parameter that is directly or indirectly responsive to the activation. Undesirable nerve activation, such as activation of the vagus or phrenic nerves, for example, may be directly sensed using electroneurogram (ENG) electrodes and circuitry to measure and/or record nerve spikes and/or action potentials in a nerve. An ENG sensor may comprise a neural cuff and/or other type or neural electrodes located on or near the nerve of interest. For example, systems and methods for direct measurement of nerve activation signals are discussed in U.S. Pat. Nos. 4,573,481 and 5,658,318 which are incorporated herein by reference in their respective entireties. The ENG may comprise a helical neural electrode that wraps around the nerve and is electrically connected to circuitry configured to measure the nerve activity. The neural electrodes and circuitry operate to detect an electrical activation (action potential) of the nerve following application of the electrical stimulation pulse.

Tissue activation not consistent with a prescribed therapy can also include anodal stimulation of cardiac tissue. For example, pacing may cause the cardiac tissue to be stimulated at the site of the anode electrode instead of the cathode electrode pacing site as expected. Cardiac signals sensed following the pacing pulse are analyzed to determine if a pacing pulse captured the cardiac tissue. Capture via anodal activation may result in erroneous detection of capture, loss of capture, unintended cardiac activation, and/or unpredictable wave propagation. Some electrode combinations may be more susceptible to anodal stimulation than other electrode combinations. As such, the occurrence of anodal stimulation is a non-beneficial parameter that does not support cardiac function and/or is not consistent with the patient's therapy.

An exemplary list of beneficial and/or non-beneficial parameters that may be sensed via the parameter sensors includes impedance, contraction duration, ventricular synchronization, activation sequence, depolarization and/or repolarization wave characteristics, intervals, responsiveness to cardiac resynchronization, electrode combination activation timing, extra-cardiac stimulation, non-cardiac muscle stimulation (ex. skeletal muscle stimulation), nerve stimulation, anodal cardiac stimulation, contractility, blood pressure, dP/dt, stroke volume, cardiac output, contraction duration, hemodynamics, ventricular synchronization, activation sequence, depolarization and/or repolarization wave characteristics, intervals, responsiveness to cardiac resynchronization, electrode combination activation timing, stimulation strength/duration relationship, among others. One or more of these sensed parameters can be used in conjunction with the methods discussed herein to select an electrode combination.

Figure 5:
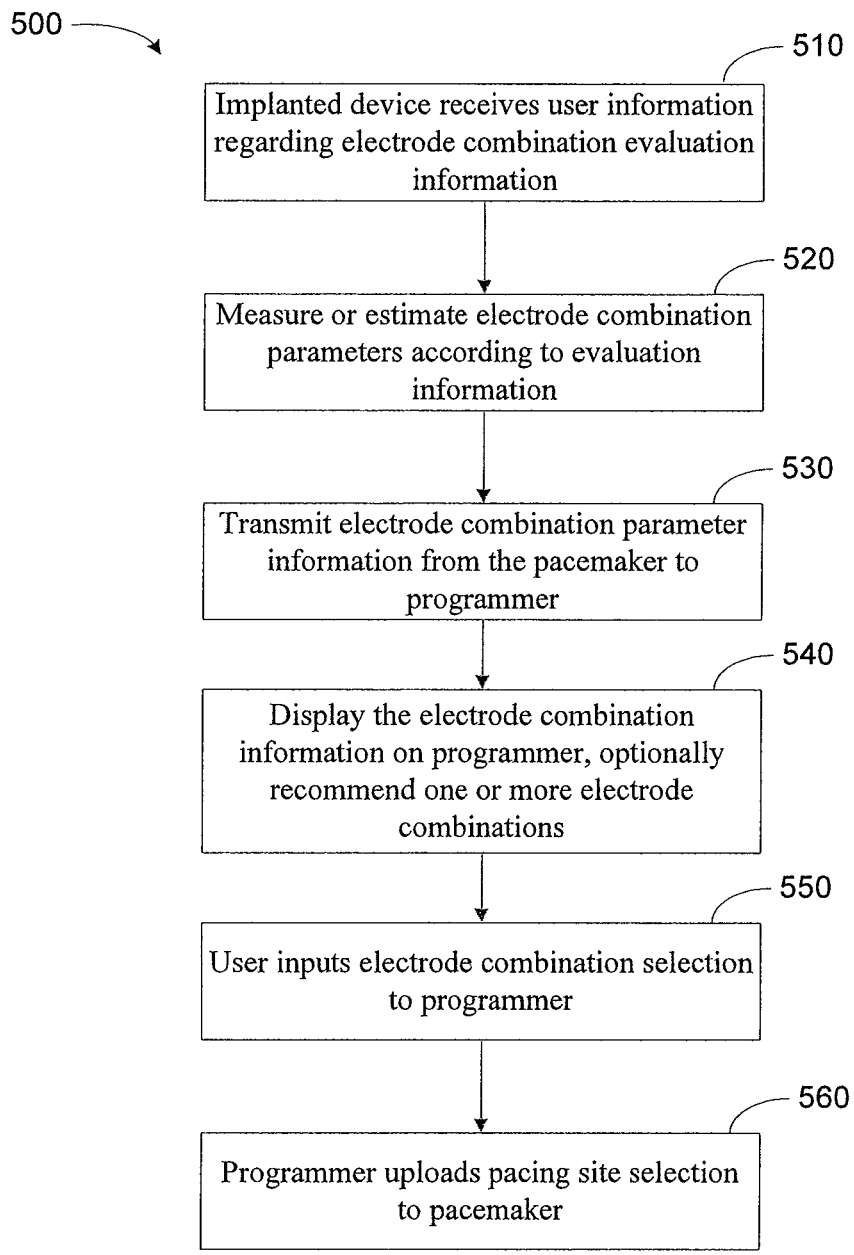
FIG. 5 is a flowchart illustrating a method of selecting one or more electrode combinations, and further exemplifying how information can be handled and managed, in accordance with embodiments of the invention.

The flowchart of FIG. 5 illustrates how information can be handled and managed according to a process 500 for selecting one or more electrode combinations. The process 500 includes an implanted device receiving 510 user information for electrode combination evaluation. The information used for electrode combination evaluation may be determined by a human.

The process 500 of FIG. 5 further includes measuring or estimating 520 electrode combination parameters identified as beneficial or non-beneficial parameters of interest. Measuring or estimating can be performed according to any method disclosed herein or known in the art.

By way of example, the received information may be the parameters of beneficial responsiveness to cardiac resynchronization and non-beneficial arrhythmia induction, among others. The responsiveness to cardiac resynchronization parameter and the arrhythmia induction parameter may then be measured or estimated 520 for a plurality of electrode combinations.

The process 500 of FIG. 5 further includes transmitting 530 electrode combination parameter information from the pacemaker to a programmer.

The process 500 of FIG. 5 further includes displaying 540 the electrode combination information on the programmer. The programmer can include a LCD screen or other means disclosed herein or known in the art for displaying information. Some or all of the electrode combination information may be displayed. The electrode combination information can be displayed as organized according to a rank, one or more groups, one or more categories, or other information organization scheme.

For example, the plurality of electrode combinations could be ranked, the electrode combination associated with the highest relative responsiveness to cardiac resynchronization therapy and the lowest relative occurrence of arrhythmia induction being ranked above electrode combinations with lower relative responsiveness to cardiac resynchronization therapy and higher occurrence of arrhythmia induction. In this way, the electrode combinations can be ranked so as to highlight those electrode combinations associated with the highest relative levels of beneficial parameters and the lowest relative levels of non-beneficial parameters, according to a prescribed therapy.

The programmer and/or the implantable device may include a processor and execute instructions stored in memory to algorithmically recommend one or more electrode combinations based on the transmitted electrode combination information. The particular recommended electrode combination or electrode combinations can be displayed by the programmer along with other electrode combinations and associated electrode combination parameter information, or the recommended electrode combination or electrode combinations may be displayed by the programmer with electrode combinations that were not recommended. The programmer may display one or more recommend electrode combinations and non-recommended electrode combinations, and visually highlight the one or more recommended electrode combinations. The programmer may display one or more recommended electrode combinations amongst other electrode combinations, but order the one or more recommended electrode combinations to indicate which electrode combination or combinations are recommended.

In addition to recommending an electrode combination and displaying the recommended electrode combination, the programmer may also give reasons why the particular electrode combination or combinations were recommended.

Although the particular process 500 of FIG. 5 states that the programmer displays the electrode combination information, other implementations are possible. For example, the electrode combination information may be displayed on a screen or printed from a device remote from the programmer.

Inputting 550 the electrode combination selection may be facilitated by a device displaying the electrode combination information, such as by a user selecting or confirming a displayed recommended electrode combination. Inputting 550 may be done by any methods disclosed herein or known in the art. In some embodiments of the invention, several electrode combination selections can be input by the user to the programmer.

The process 500 of FIG. 5 further includes the programmer 560 uploading an electrode combination selection to a pacemaker. The pacemaker of step 560 could be the implanted device of step 510. Uploading can be facilitated by the same means used to facilitate the implanted device receiving the user criteria, and/or transmitting the electrode combination parameter information.

Figure 6:
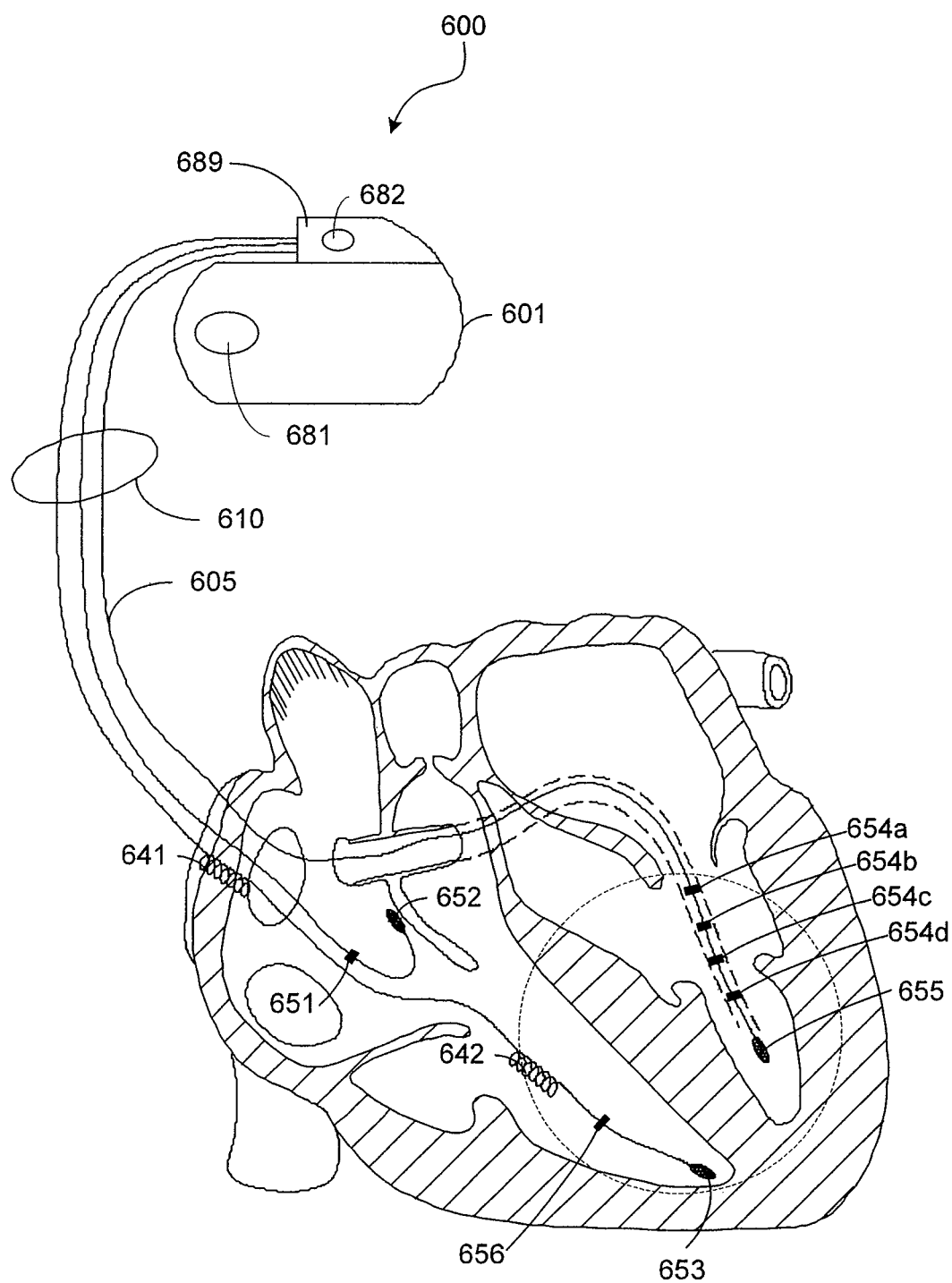
FIG. 6 is a therapy device incorporating circuitry capable of implementing electrode combination selection techniques in accordance with embodiments of the invention.

The therapy device 600 illustrated in FIG. 6 employs circuitry capable of implementing the electrode combination selection techniques described herein. The therapy device 600 includes CRM circuitry enclosed within an implantable housing 601. The CRM circuitry is electrically coupled to an intracardiac lead system 610. Although an intracardiac lead system 610 is illustrated in FIG. 6, various other types of lead/electrode systems may additionally or alternatively be deployed. For example, the lead/electrode system may comprise and epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 610 are inserted into the patient's heart. The lead system 610 includes cardiac pace/sense electrodes 651-656 positioned in, on, or about one or more heart chambers for sensing electrical signals from the patient's heart and/or delivering pacing pulses to the heart. The intracardiac sense/pace electrodes 651-656, such as those illustrated in FIG. 6, may be used to sense and/or pace one or more chambers of the heart, including the left ventricle, the right ventricle, the left atrium and/or the right atrium. The CRM circuitry controls the delivery of electrical stimulation pulses delivered via the electrodes 651-656. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes to support cardiac function consistent with a prescribed therapy.

The lead system 610 includes defibrillation electrodes 641, 642 for delivering defibrillation/cardioversion pulses to the heart.

The left ventricular lead 605 incorporates multiple electrodes 654a-654d and 655 positioned at various locations within the coronary venous system proximate the left ventricle. Stimulating the ventricle at multiple locations in the left ventricle or at a single selected location may provide for increased cardiac output in a patients suffering from congestive heart failure (CHF), for example, and/or may provide for other benefits. Electrical stimulation pulses may be delivered via the selected electrodes according to a timing sequence and output configuration that enhances cardiac function. Although FIG. 6 illustrates multiple left ventricle electrodes, in other configurations, multiple electrodes may alternatively or additionally be provided in one or more of the right atrium, left atrium, and right ventricle.

Portions of the housing 601 of the implantable device 600 may optionally serve as one or more multiple can 681 or indifferent 682 electrodes. The housing 601 is illustrated as incorporating a header 689 that may be configured to facilitate removable attachment between one or more leads and the housing 601. The housing 601 of the therapy device 600 may include one or more can electrodes 681. The header 689 of the therapy device 600 may include one or more indifferent electrodes 682. The can 681 and/or indifferent 682 electrodes may be used to deliver pacing and/or defibrillation stimulation to the heart and/or for sensing electrical cardiac signals of the heart.

Communications circuitry is disposed within the housing 601 for facilitating communication between the CRM circuitry and a patient-external device, such as an external programmer or advanced patient management (APM) system. The therapy device 600 may also include sensors and appropriate circuitry for sensing a patient's metabolic need and adjusting the pacing pulses delivered to the heart and/or updating the electrode combination selection to accommodate the patient's metabolic need.

In some implementations, an APM system may be used to perform some of the processes discussed here, including evaluating, estimating, comparing, ordering, selecting, and updating, among others. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference in each of their respective entireties.

In certain embodiments, the therapy device 600 may include circuitry for detecting and treating cardiac tachyarrhythmia via defibrillation therapy and/or anti-tachyarrhythmia pacing (ATP). Configurations providing defibrillation capability may make use of defibrillation coils 641, 642 for delivering high energy pulses to the heart to terminate or mitigate tachyarrhythmia.

CRM devices using multiple electrodes, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pacing pulses between selected electrode combinations within a heart chamber during different cardiac cycles.

Figure 7:
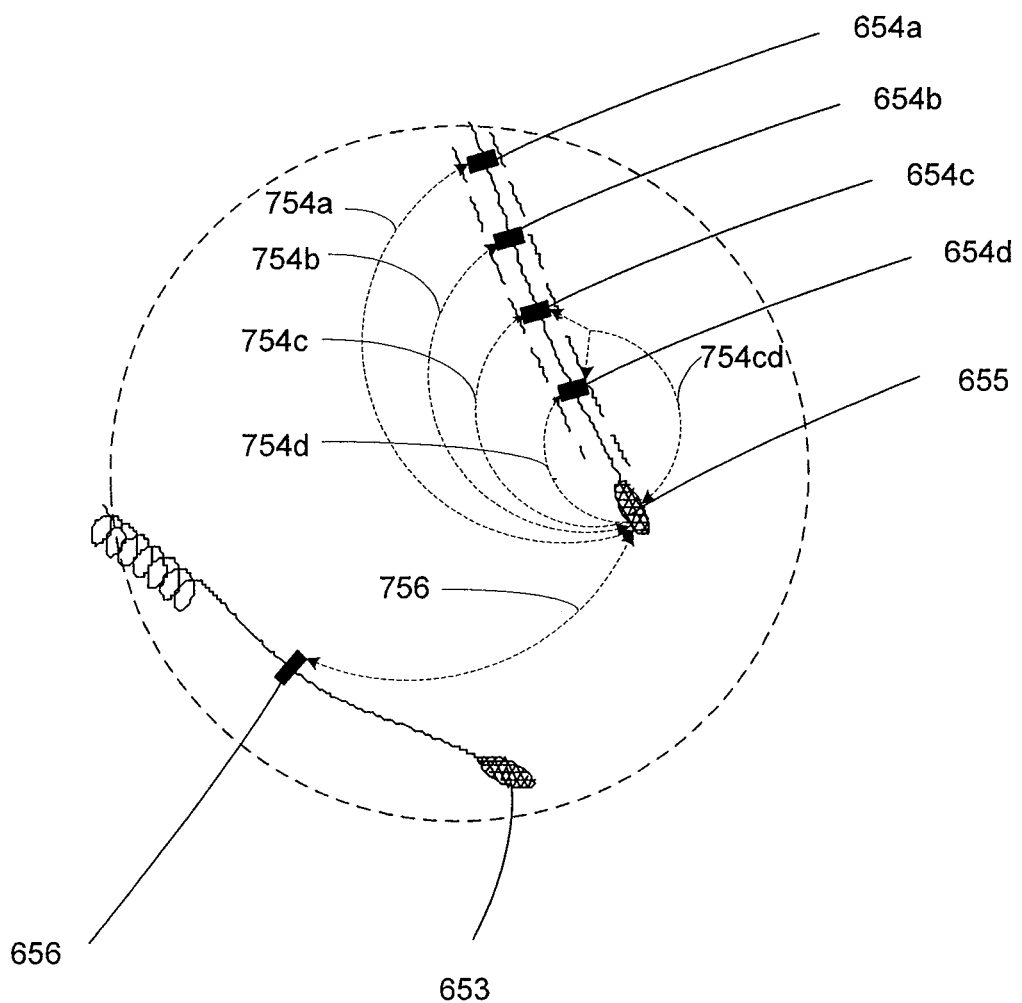
FIG. 7 shows an enlarged view of various pacing configurations that may be used in connection with electrode combination selection in accordance with embodiments of the invention.

FIG. 7 illustrates an enlarged view of the area delineated by the dashed line circle in FIG. 6. FIG. 7 illustrates various pacing configurations 754a, 754b, 754c, 754d, 754cd, and 756 that may be used to deliver pacing pulses. Each of the pacing configurations 754a, 754b, 754c, 754d, 754cd, and 756 includes a common cathode electrode 655. Pacing configuration 754a is defined between cathode electrode 655 and anode electrode 654a; pacing configuration 754b is defined between cathode electrode 655 and anode electrode 654b; pacing configuration 754c is defined between cathode electrode 655 and anode electrode 654c; pacing configuration 754d is defined between cathode electrode 655 and anode electrode 654d; pacing configuration 756 is defined between cathode electrode 655 and anode electrode 656. In some configurations, the pacing configuration cathode, or the pacing configuration anode, or both, may comprise multiple electrodes. For example, pacing configuration 754cd includes cathode electrode 655 and anode electrodes 654c and 654d.

Each of the pacing configurations discussed above correspond to an electrode combination, and each pacing configuration and electrode combination likewise correspond to a pacing site and/or vector. Delivering an identical electrical therapy using each electrode combination can elicit a different response from the patient. For example, therapy delivered at one electrode combination may be more likely to capture a chamber than another site. Also, therapy delivered using one electrode combination may be more likely to stimulate the diaphragm than another site. Therefore, it is important to identify the electrode combination through which optimum therapy can be delivered. In some cases, the optimum electrode combination for therapy is one that causes the desired response, using the smallest amount of power (such as battery storage), that does not cause undesirable stimulation. For example, an optimal electrode combination may be an electrode combination through which a delivered therapy captures the intended chamber requiring the smallest amount of voltage and current that does not stimulate the diaphragm or skeletal muscles, or other extra-cardiac tissue.

Figure 8:
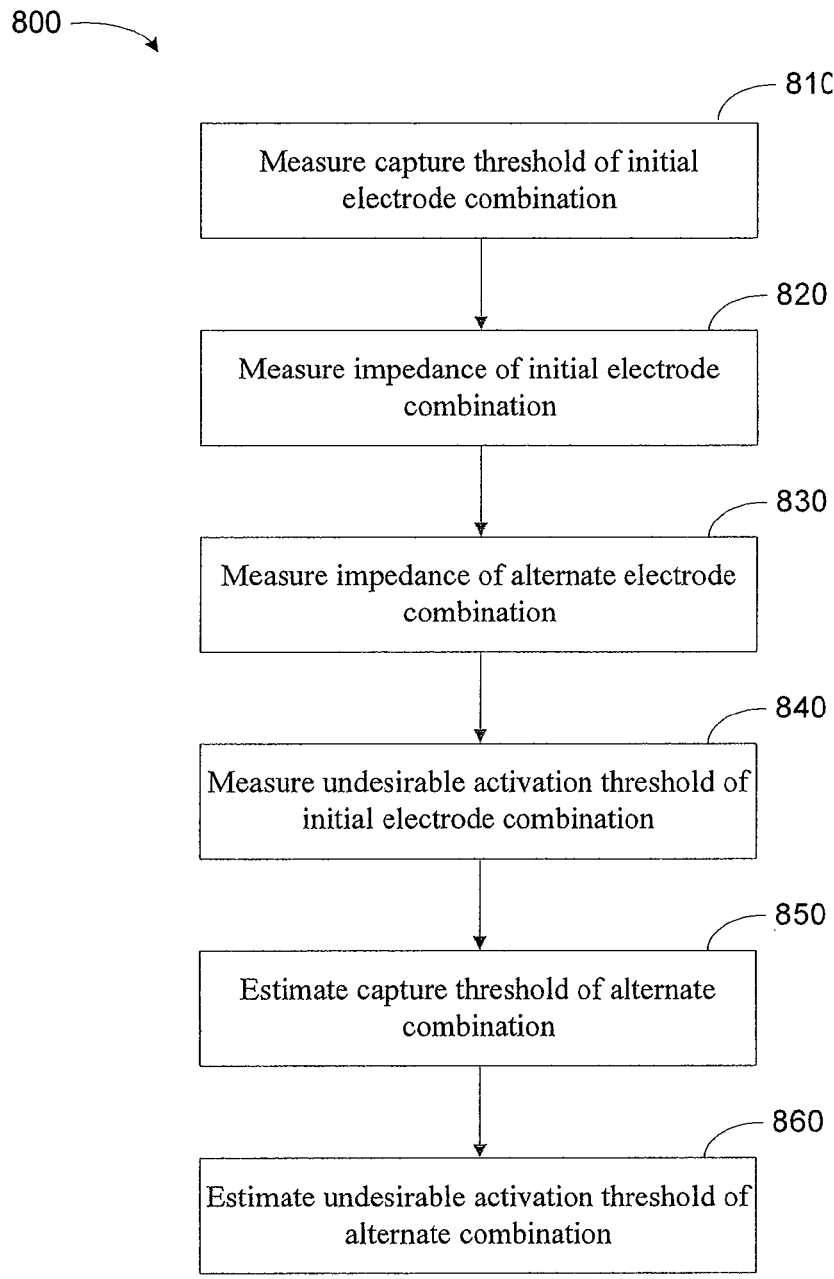
FIG. 8 is a flowchart illustrating a method of estimating parameters in accordance with embodiments of the invention.

The flowchart of FIG. 8 illustrates a process 800 for estimating parameters, specifically, both beneficial (e.g., capture) and non-beneficial (e.g., undesirable activation) parameters. The process 800 includes measuring 810 a capture threshold of an initial electrode combination. The procedure for measuring 810 a capture threshold for the initial electrode combination can be done according to any capture threshold measuring methods disclosed herein or known in the art.

The process 800 of FIG. 8 further includes measuring 820 the impedance of the initial electrode combination. The impedance of the initial electrode combination may be measured with the capture threshold measurement of the initial electrode combination.

Any method for measuring impedance for each electrode combination may be used. One illustrative example of techniques and circuitry for determining the impedance of an electrode combination is described in commonly owned U.S. Pat. No. 6,076,015 which is incorporated herein by reference in its entirety.

In accordance with this approach, measurement of impedance involves an electrical stimulation source, such as an exciter. The exciter delivers an electrical excitation signal, such as a strobed sequence of current pulses or other measurement stimuli, to the heart between the electrode combination. In response to the excitation signal provided by an exciter, a response signal, e.g., voltage response value, is sensed by impedance detector circuitry. From the measured voltage response value and the known current value, the impedance of the electrode combination may be calculated.

The process 800 of FIG. 8 further includes measuring 830 the impedance of an alternate electrode combination. The measuring step 830 could be repeated for a plurality of different alternate electrode combinations.

The process 800 of FIG. 8 further includes measuring 840 an undesirable activation threshold of the initial electrode combination. The procedure for measuring 840 the undesirable activation threshold of the initial electrode combination may be similar to the procedure for measuring 810 the capture threshold of the initial electrode combination, and may be done concurrently with the measuring 810 of the capture threshold of the initial electrode combination.

Undesirable activation threshold measuring may be performed by iteratively increasing, decreasing, or in some way changing a voltage, current, duration, and/or some other therapy parameter between a series of test pulses that incrementally increase in energy level. One or more sensors can monitor for undesirable activation immediately after each test pulse is delivered. Using these methods, the point at which a parameter change causes undesirable activation can be identified as an undesirable activation threshold.

By way of example and not by way of limitation, the undesirable activation threshold for an electrode combination may be measured by delivering first test pulse using the initial electrode combination. During and/or after each test pulse is delivered, sensors can monitor for undesirable activation. For example, an accelerometer may monitor for contraction of the diaphragm indicating that the test pulse stimulated the phrenic nerve and/or diaphragm muscle. If no phrenic nerve and/or diaphragm muscle activation is detected after delivery of a test pulse, then the test pulse is increased a predetermined amount and another test pulse is delivered. This scanning process of delivering, monitoring, and incrementing is repeated until phrenic nerve and/or diaphragm muscle activation is detected. One or more of the test pulse energy parameters at which the first undesirable activation is detected, such as voltage, can be considered to be the undesirable activation threshold.

The process 800 of FIG. 8 further includes estimating 850 a capture threshold of the alternate electrode combination. Estimating 850 the capture threshold of the alternate electrode combination can be performed by using the capture threshold and the impedance of the initial electrode combination and the impedance of the alternate electrode combination.

Estimation of the capture threshold of the alternate electrode combination in accordance with some embodiments described herein is based on the assumption that for a given pulse width, the capture threshold voltage for the initial electrode combination and the capture threshold voltage for the alternate electrode combination require an equal amount of current, energy or charge. The relationship between the capture threshold voltage and current for each electrode combination can be defined by Ohm's law as follows:

$$V_{th} = I_{th} Z, \quad [1]$$

where $V_{th}$ is the capture threshold voltage of the electrode combination, $I_{th}$ is the capture threshold current of the electrode combination, and $Z$ is the impedance of the electrode combination.

For the initial electrode combination, the relationship between the capture threshold voltage and current may be expressed as:

$$V_{th\text{-}in} = I_{th\text{-}in} Z_{in} \quad [2]$$

where, $V_{th\text{-}in}$ is the capture threshold voltage of the initial electrode combination, $I_{th\text{-}in}$ is the capture threshold current of the initial electrode combination, and $Z_{in}$ is the impedance of the initial electrode combination.

For the alternate electrode combination, the relationship between the capture threshold voltage and current may be expressed as:

$$V_{th\text{-}ex} = I_{th\text{-}ex} Z_{ex} \quad [3]$$

where, $V_{th\text{-}ex}$ is the capture threshold voltage of the alternate electrode combination, $I_{th\text{-}ex}$ is the capture threshold current of the alternate electrode combination, and $Z_{ex}$ is the impedance of the alternate electrode combination.

As previously stated, in some embodiments, the capture threshold current of two electrode combinations having a common electrode is assumed to be about equal, or, $I_{th\text{-}in} = I_{th\text{-}ex}$.

The relationship between the alternate and initial capture threshold voltages may then be expressed as:

$$V_{th\text{-}ex} = \frac{V_{th\text{-}in}}{Z_{in}} Z_{ex} \quad [4]$$

By the processes outlined above $V_{th\text{-}in}$, $Z_{in}$, and, $Z_{ex}$ are measured parameters, and the capture threshold voltage may be estimated based on these measured parameters.

The accuracy of an estimation calculation of a capture threshold for a particular electrode combination may be increased if the measured electrode combination has the same polarity as the electrode combination for which the capture threshold is being estimated. Methods for parameter estimation, including capture threshold estimation, are disclosed in U.S. Pat. No. 7,680,536, herein incorporated by reference in its entirety.

The process 800 of FIG. 8 further includes estimating 860 an undesirable activation threshold of the alternate electrode combination. Estimating 860 the undesirable activation threshold of the alternate electrode combination can be performed by using the undesirable activation threshold and the impedance of the initial electrode combination and the impedance of the alternate electrode combination. Estimating 850 the undesirable activation threshold of the alternative electrode combination can be performing using methods similar to estimating a capture threshold, as discussed and referenced herein.

Estimating a threshold, such as estimating a capture threshold and/or an undesirable activation threshold, instead of measuring the same, can provide several advantages. For example, in some circumstances, measuring and estimating of some thresholds for a plurality of electrode combinations can be done faster than measuring the threshold for each electrode combination of the plurality of electrode combinations, as one or more test pulses do not need to be delivered for each electrode combination. Additionally, a test pulse can be uncomfortable for a patient to experience, and therefore minimizing the number of test pulses can be preferable.

Appropriate selection of the energy parameters and an electrode combination that produce the desired activation that supports cardiac and avoid the undesirable activation, consistent with a prescribed therapy, can involve the use of strength-duration relationships measured or otherwise provided. The selection of an electrode combination may involve evaluating the cardiac response across ranges of one or more of pulse width, pulse amplitude, frequency, duty cycle, pulse geometry, and/or other energy parameters.

Capture is produced by pacing pulses having sufficient energy to produce a propagating wavefront of electrical depolarization that results in a contraction of the heart tissue. The energy of the pacing pulse is a product of two energy parameters—the amplitude of the pacing pulse and the duration of the pulse. Thus, the capture threshold voltage over a range of pulse widths may be expressed in a strength-duration plot 910 as illustrated in FIG. 9.

Undesirable activation by a pacing pulse is also dependent on the pulse energy. The strength-duration plot 920 for undesirable activation may have a different characteristic from the capture strength-duration and may have a relationship between pacing pulse voltage and pacing pulse width.

A CRM device, such as a pacemaker, may have the capability to adjust the pacing pulse energy by modifying either or both the pulse width and the pulse amplitude to produce capture. Identical changes in pacing pulse energy may cause different changes when applied to identical therapies using different electrode combinations. Determining a strength-duration plot 910 for a plurality of electrode combinations can aid in selecting an electrode combination, as the strength-duration plots can be a basis for comparison of beneficial and non-beneficial pacing characteristics and parameters.

Figure 9:
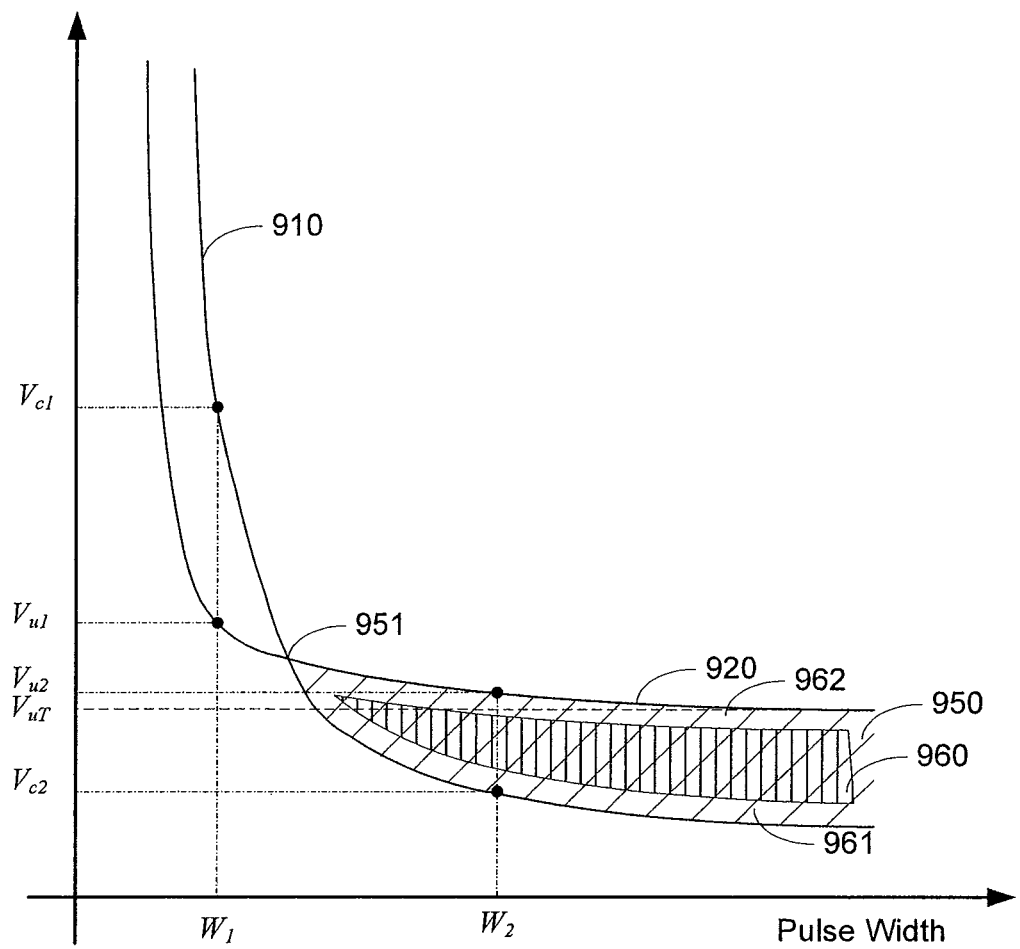
FIG. 9 is a graph illustrating various aspects of a strength-duration plot for a parameter that supports cardiac function and a strength-duration plot for a parameter that does not support cardiac function that may be used to select an electrode combination for a therapeutic electrical stimulation in accordance with embodiments of the invention.

FIG. 9 provides graphs illustrating a strength-duration plot 910 associated with capture and a strength-duration plot 920 associated with an undesirable activation. A pacing pulse having a pulse width of $W_1$ requires a pulse amplitude of $V_{c1}$ to produce capture. A pacing pulse having pulse width $W_1$ and pulse amplitude $V_{c1}$ exceeds the voltage threshold, $V_{u1}$, for an undesirable activation. If the pulse width is increased to $W_2$, the voltage required for capture, $V_{c2}$, is less than the voltage required for undesirable activation, $V_{u2}$. Therefore, pacing pulses can be delivered at the pacing energy associated with $W_2$, $V_{c2}$ to provide capture of the heart without causing the undesirable activation. The shaded area 950 between the plots 910, 920 indicates the energy parameter values that may be used to produce capture and avoid undesirable activation.

If multiple-point strength duration plots are known for capture and undesirable activation, the energy parameters for a particular electrode combination may be determined based on these two plots. For example, returning to FIG. 9, the area 950 to the right of the intersection 951 of the strength-duration plots 910, 920 defines the set of energy parameter values that produce capture while avoiding undesirable stimulation. Energy parameter values that fall within this region 950, or within a modified region 960 that includes appropriate safety margins for pacing 961 and undesirable activation 962, may be selected.

According to some embodiments of the present invention, various parameters and/or characteristics, such as ranges, windows, and/or areas, of the plots of FIG. 9 may be used in selecting an electrode combination. For example, equivalent strength-duration plots 910 and strength-duration plot 920 associated with an undesirable activation may be generated for each of a plurality of electrode combinations. Then the respective areas 960 and/or 950 may be compared between the electrode combinations, the comparison used to determine an order for the electrode combinations. Because the parameters represented by area 960 represent the available ranges of voltage and pulse width within an acceptable safety margin, electrode combinations with relatively large area 960 may be favorably ranked in an electrode combination order. A comparison can also be made between various electrode combinations of the voltage ranges, at a specific pulse width, that captures the heart without causing undesirable stimulation, with priority in the order being given to electrode combinations with the largest ranges.

Strength-duration plots, such as plots 910 and 920, can provide other parameters for evaluating and comparing to order electrode combinations and select an electrode combination. For example, criteria for selecting an electrode combination may specify that the selected combination is the combination with the lowest capture threshold that does not exceed a certain pulse width.

Methods and systems for determining and using strength-duration relationships are described in U.S. Patent Publication No. 2008/0071318, which is incorporated herein by reference in its entirety.

Figure 10:
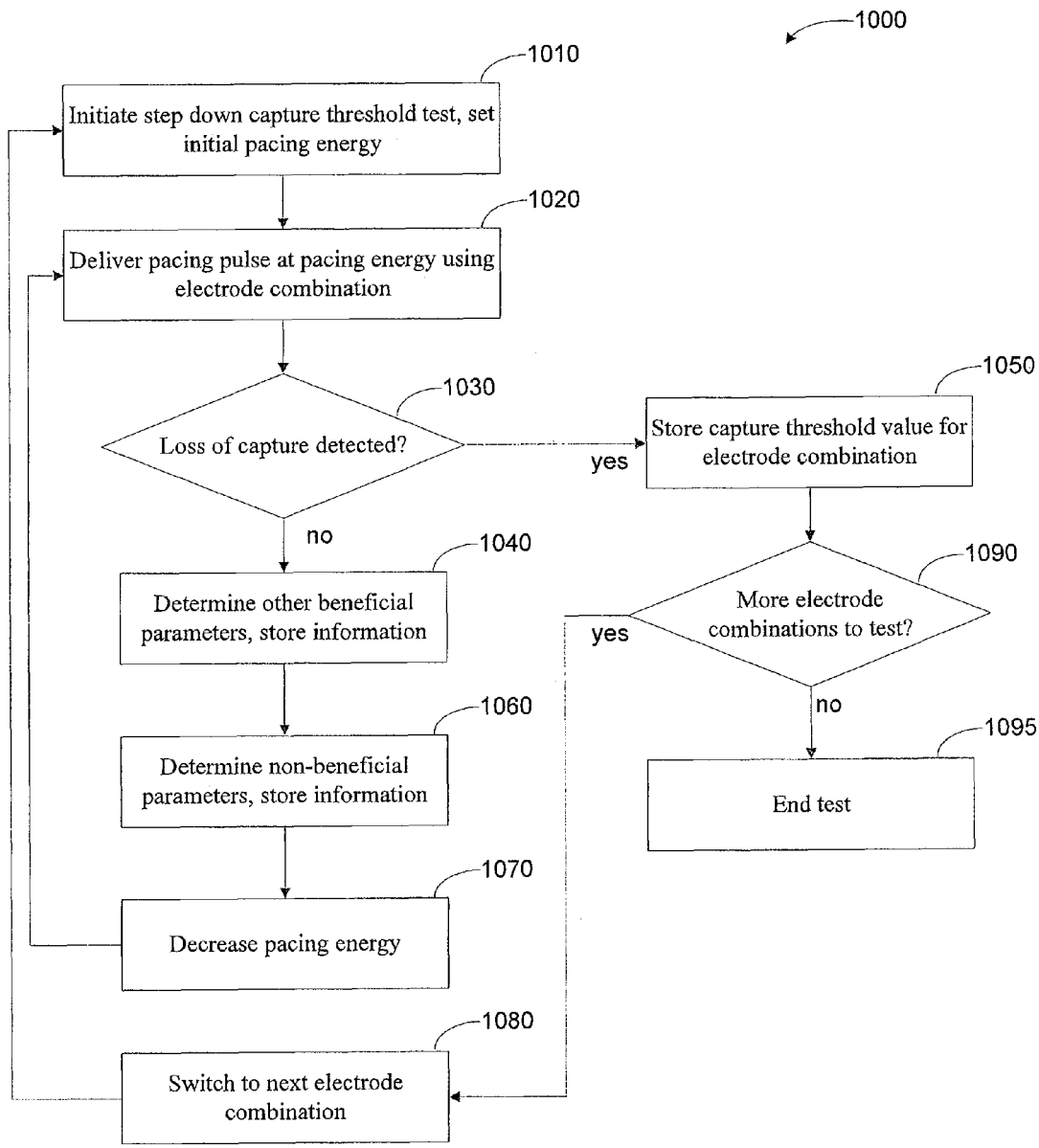
FIG. 10 is a flowchart illustrating a method of evaluating a plurality of electrode combinations, and further exemplifying how capture thresholds for a plurality of electrode combinations can be determined, in accordance with embodiments of the invention.

The flowchart of FIG. 10 illustrates a process 1000 for determining capture thresholds for a plurality of electrode combinations. The process 1000 includes initiating 1010 a step down threshold test, and setting an initial pacing energy. The process 1000 further includes delivering 1020 a pacing pulse at pacing energy to an electrode combination. The electrode combination may be an initial electrode combination. The pacing energy may be the initial pacing energy, particularly in the case where step 1020 has not been previously performed.

After delivery 1020 of the pacing pulse, the process monitors to determine whether loss of capture is detected 1030. If loss of capture is detected, then the process 1000 proceeds to determining 1040 other beneficial parameters, and storing the beneficial parameter information. The other beneficial parameters determined could be any of the beneficial parameters discussed herein or known in the art that support cardiac function consistent with a prescribed therapy. Examples of such beneficial parameters include electrode combination responsiveness to CRT, low battery consumption, and cardiac output, among other parameters.

The process determines 1060 non-beneficial parameters, and stores the non-beneficial parameter information. The non-beneficial parameters determined could be any of the non-beneficial parameters discussed herein or known in the art. Examples of such non-beneficial parameters include extra-cardiac stimulation and anodal stimulation, among other parameters.

After determining 1060 non-beneficial parameters, the process 1000 proceeds to decrease 1070 the electrode combination energy. After the electrode combination energy is decreased 1070, a pacing pulse is delivered 1020 using the electrode combination using the energy level to which the energy level was decreased. In this way, steps 1020, 1030, 1040, 1060, and 1070 can be repeated, decreasing 1070 the pacing energy for the electrode combination until loss of capture is detected 1030. As such, steps 1010, 1020, 1030, 1040, 1060, and 1070 can scan for a capture threshold, the capture threshold being stored 1050 in memory for the electrode combination once it has been identified by a detected loss of capture 1030.

After detecting loss of capture 1030 and storing 1050 the capture threshold for the electrode combination, the process 1000 evaluates whether there are more electrode combinations to test 1090. If there are more electrode combinations to test, then the process 1000 switches 1080 to the next electrode combination and repeats steps 1020, 1030, 1040, 1060, and 1070 to determine the capture threshold for the next electrode combination. When there are no more electrode combinations to test 1090, the test ends 1095. As such, process 1000 can be used to determine the capture threshold, beneficial parameters, and non-beneficial parameters for one or more of a plurality of electrode combinations. This information can then be used in conjunction with other methods disclosed herein to select an electrode combination, among other things.

Although the process 1000 of FIG. 10 used a step down capture threshold test, in other implementations, the capture threshold test may involve a step-up capture threshold test, a binary search test, or may involve other capture threshold testing methods as are known in the art. Similar methods to those discussed herein can be used to determine other parameter thresholds.

The capture threshold of an electrode combination may change over time due to various physiological effects. Testing the capture threshold for a particular electrode combination may be implemented periodically or on command to ensure that the pacing energy delivered to the particular electrode combination remains sufficient to produce capture.

Figure 11:
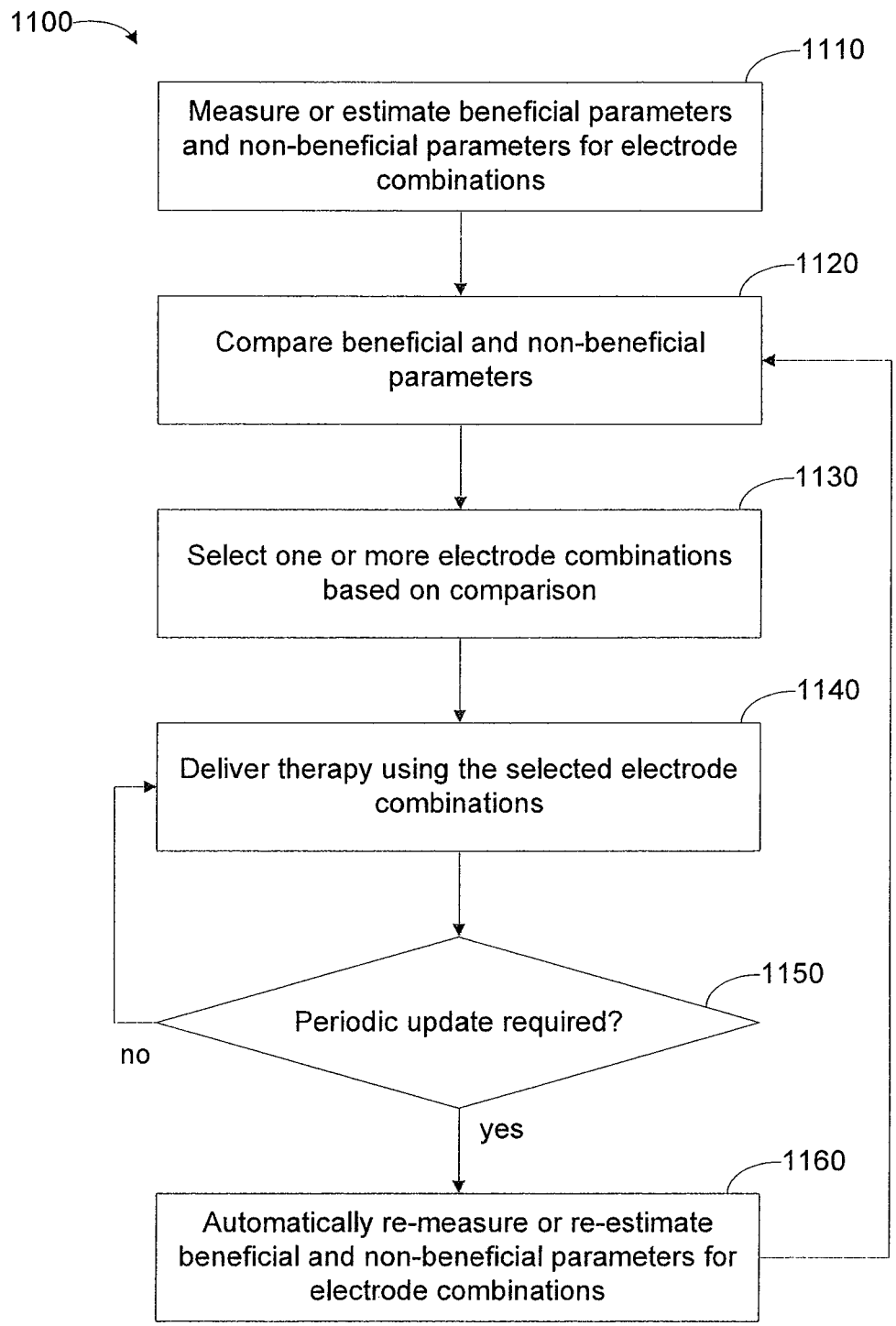
FIG. 11 is a flowchart illustrating a method of automatically updating a therapy electrode combination after an initial selection in accordance with embodiments of the invention.

The flowchart of FIG. 11 illustrates a process 1100 for automatically updating a therapy electrode combination after an initial selection. Beneficial parameters and non-beneficial parameters are measured or estimated 1110 for a plurality of electrode combinations. Step 1110 can be scheduled to occur at implant, or could be initiated after implant. As in other embodiments discussed herein, the beneficial parameters can be parameters that support cardiac function consistent with a prescribed therapy and the non-beneficial parameters can be parameters that do not support cardiac function consistent with a prescribed therapy.

After the beneficial and non-beneficial parameters are evaluated 1110, the beneficial and non-beneficial parameters are compared 1120. Based on the comparison, electrode combinations are selected 1130. Therapy is then delivered 1140 using the selected electrode combinations. After therapy is delivered 1140 using the selected electrode combinations, the process 1100 evaluates whether a periodic update is required 1150. A periodic update could be mandated by a programmed update schedule, or may be performed upon command.

If no periodic update is required, then therapy continues to be delivered 1140 using the selected electrode combinations. However, if a periodic update is required, then the process automatically re-measures or re-estimates 1160 beneficial and non-beneficial parameters for the plurality of electrode combinations. Automatically re-measuring or re-estimating 1160 could be performed by a method similar or identical to the method used to measure or estimate beneficial parameters 1110 at implant. After re-measuring or re-estimating the beneficial and non-beneficial parameters, the re-measured or re-estimated parameters are compared 1120, such that electrode combinations may then be selected 1130 and used to deliver 1140 a therapy.

Figure 12:
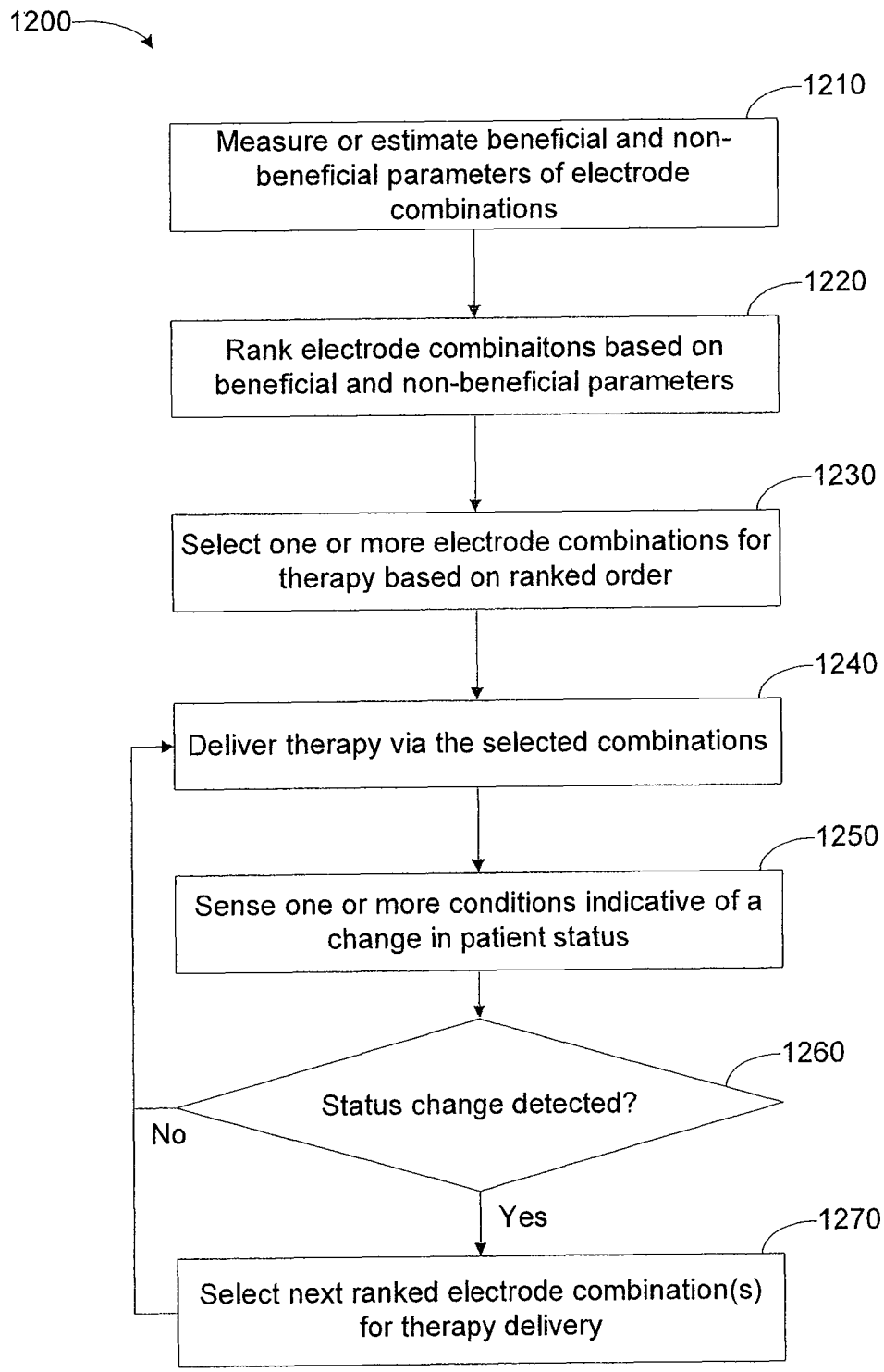
FIG. 12 is a flowchart illustrating a method of selecting an electrode combination, and further exemplifying ranking electrode combinations and changing the electrode combination being used for therapy delivery using the ranking, in accordance with embodiments of the invention.

The flowchart of FIG. 12 illustrates a process 1200 for ranking electrode combinations and changing the electrode combination being used for therapy delivery using the ranking. The process 1200 begins with measuring or estimating 1210 beneficial parameters and non-beneficial parameters for a plurality of electrode combinations. As in other embodiments discussed herein, the beneficial parameters can be parameters that support cardiac function consistent with a prescribed therapy and the non-beneficial parameters can be parameters that do not support cardiac function consistent with a prescribed therapy.

After the beneficial and non-beneficial parameters are measured or estimated 1210, the beneficial and non-beneficial parameters are ranked 1220.

Ranking can include establishing a hierarchical relationship between a plurality of electrode combinations based on parameters. In such embodiments, the highest ranked electrode combination maybe the electrode combination with most favorable beneficial parameter and non-beneficial parameter values relative to other electrode combinations, which are likewise ordered in a rank.

Based on the ranking, electrode combinations are selected 1230. Therapy is then delivered 1240 using the selected electrode combinations.

After therapy is delivered 1240 using the selected electrode combinations, the process 1200 senses 1250 for one or more conditions indicative of a change in the patient's status. In some embodiments of the invention, a sensed change in the patient status could include a sensed change in activity level, posture, respiration, electrode position, body fluid chemistry, blood or airway oxygen level, blood pressure, hydration, hemodynamics, or electrode combination impedance, among other events.

If no status change is detected 1260, then therapy continues to be delivered 1240 using the selected electrode combinations. However, if a status change is detected 1260, then the process selects 1270 the next ranked electrode combination or sites for therapy delivery and delivers 1240 therapy via the selected site or sites. According to the particular process 1200 of FIG. 12, no re-measuring or re-estimating of parameters is needed, as the process uses the ranking determined in step 1220.

Although the embodiment of FIG. 12 uses a ranking method to order the electrode combinations, other ordering methods are contemplated within the scope of the present invention. Ordering may include grouping, attributing, categorizing, or other processes that are based on parameter evaluations.

Ordering can include grouping a plurality of electrode combinations according to one or more of the parameters that support cardiac function and one or more of the parameters that do not support cardiac function, consistent with a prescribed therapy. For example, the electrode combinations of the plurality of electrode combinations can be grouped in various categories, each category associated with a different type of detected undesirable stimulation (ex. phrenic nerve, anodal stimulation, excessive impedance) and/or parameter that does support cardiac function (ex. low capture threshold; low impedance).

In some applications, it is desirable to select pacing electrodes based on a number of interrelated parameters. For example, in cardiac resynchronization therapy (CRT) which involves left ventricular pacing, it is desirable to deliver pacing pulses that capture the heart tissue to produce a left ventricular contraction without unwanted stimulation to other body structures. However, the pacing therapy may be ineffective or less effective if pacing is delivered to a site that is a non-responder site to CRT. Thus, selection of a responder site for therapy delivery should also be taken into account. In some embodiments, the electrode selection may consider several inter-related parameters, ordering, ranking, grouping and/or recommending the electrode combinations to achieve specific therapeutic goals.

In some embodiments, the ordering, ranking, grouping and/or recommending may be performed using a multivariable optimization procedure. Electrode selection using some level of algorithmic automaticity is particularly useful when a large number of electrode combinations are possible in conjunction with the evaluation of several parameters.

Ordering can be based on the evaluations of any number of different parameters that support cardiac function consistent with a prescribed therapy and any number of parameters that do not support cardiac function consistent with a prescribed therapy. For example, ordering can be based on a comparison of the respective evaluations of two different parameters that each support cardiac function consistent with a prescribed therapy and one or more parameters that do not support cardiac function consistent with a prescribed therapy, each evaluation conducted for each electrode combination of a plurality of electrode combinations. In this example, the two different parameters that support cardiac function consistent with a prescribed therapy could be left ventricular capture threshold and improved hemodynamics, while the parameter that does not support cardiac function consistent with a prescribed therapy could be phrenic nerve activation.

Evaluating, ordering, and other comparisons of the present invention based on multiple parameters can include one, two, three, four, five, or more different parameters that support cardiac function consistent with a prescribed therapy and one, two, three, four, five, or more different parameters that do not support cardiac function consistent with a prescribed therapy.

In some embodiments of the invention, not all possible electrode combinations will be evaluated. For example, a very high capture threshold associated with a first electrode combination may indicate that another electrode combination using the cathode or the anode of the first electrode combination may as well have a very high capture threshold. In such cases, evaluations of parameters for electrode combinations using those electrodes and/or electrodes proximate one of those electrodes will not be conducted. Forgoing evaluation of those electrode combinations likely to perform poorly based on the performance of similar electrode combinations can save evaluation time, energy, and avoid unnecessary stimulation while testing patient response. The forgoing of evaluating certain electrode combinations can be based on any of the other parameters discussed herein.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method comprising:
    delivering electrical stimulation to a patient's heart using a plurality of cardiac electrodes supported inside the patient by one or more at least partially implanted leads and an evaluation unit having an analyzer circuit that is external of the patient and attached to the one or more leads;
    receiving user-determined electrode combination selection criteria from a user via the evaluation unit;
    evaluating, for each electrode combination of a plurality of electrode combinations of the plurality of cardiac electrodes, one or more first parameters and one or more second parameters produced by the electrical stimulation delivered using the electrode combination, the first parameters supportive of cardiac function consistent with a prescribed therapy and the second parameters not supportive of cardiac function consistent with the prescribed therapy;
    selecting one or more electrode combinations of the plurality of cardiac electrodes based, at least in part, on the user-determined electrode combination selection criteria; and
    programming an implantable pacing circuit to deliver a cardiac pacing therapy that preferentially uses the selected one or more electrode combinations relative to other electrode combinations of the plurality of cardiac electrodes.

2. The method of claim 1, wherein evaluating the one or more first parameters comprises evaluating a capture threshold for each of the plurality of electrode combinations, and wherein evaluating the one or more second parameters comprises evaluating extra-cardiac stimulation for each of the plurality of electrode combinations.

3. The method of claim 1, wherein evaluating the one or more first parameters comprises evaluating a responsiveness to cardiac resynchronization.

4. The method of claim 1, wherein evaluating the one or more second parameters comprises detecting at least one of unintended nerve stimulation and unintended muscle stimulation.

5. The method of claim 1, wherein the user-determined electrode combination selection criteria indicate one or more boundary conditions comprising one or more of a maximum pulse amplitude at which the implantable pacing circuit is programmed to deliver, a minimum pulse amplitude at which the implantable pacing circuit is programmed to deliver, a maximum pulse width at which the implantable pacing circuit is programmed to deliver, a minimum pulse amplitude at which the implantable pacing circuit is programmed to deliver.

6. The method of claim 1, wherein the user-determined electrode combination selection criteria indicate which electrode combinations of the plurality of cardiac electrodes will be evaluated.

7. The method of claim 1, further comprising:
    determining a ranking for at least some of the electrode combinations of the plurality of electrode combinations based on the evaluations of the one or more first parameters and the one or more second parameters for each electrode combination of the plurality of electrode combinations, wherein the one or more electrode combinations of the plurality of cardiac electrodes based are selected based, at least in part, on the ranking.

8. The method of claim 7, further comprising detecting a change in a patient's condition, wherein programming the implantable pacing circuit to deliver the cardiac pacing therapy further comprises programming the implantable pacing circuit to switch delivery of the cardiac pacing therapy from a first prioritized electrode combination of the ranking to a lower prioritized electrode combination of the ranking in response to the detected change in the patient's condition.

9. The method of claim 7, wherein determining the ranking of at least some electrode combinations comprises ranking at least some electrode combinations based on one or more of capture threshold, therapy energy consumption, undesirable activation of nerve or muscle tissue, anodal cardiac stimulation, degree of responsiveness to resynchronization therapy, impedance, cardiac contractility, electrode combination activation timing, cardiac output, stroke volume, dP/dt, hemodynamics, and historical success of therapy using the electrode combinations.

10. The method of claim 1, wherein evaluating the one or more first parameters comprises evaluating for each electrode combination two or more different first parameters associated with electrical stimulation delivered using the corresponding electrode combination, the two or more different first parameters supportive of cardiac function consistent with the prescribed therapy.

11. The method of claim of claim 1, further comprising:
    displaying for each of two or more of the plurality of electrode combinations, one or more of the first parameters and one or more of the second parameters on an electronic display;
    accepting a user input from a user; and
    ranking the two or more of the plurality of electrode combinations on the display based, at least in part, on the user input and the evaluations of the first parameters and the second parameters for each of the two or more of the plurality of electrode combinations.

12. The method of claim 1, further comprising detecting a change in a patient's condition, wherein programming the implantable pacing circuit to deliver the cardiac pacing therapy further comprises programming the implantable pacing circuit to switch delivery of the cardiac pacing therapy from a first electrode combination to a second electrode combination based on the evaluations of the one or more first parameters and the one or more second parameters for each electrode combination of the plurality of electrode combinations in response to the detected change in the patient's condition.

13. A method comprising:
    delivering electrical stimulation to a patient's heart using a plurality of cardiac electrodes;
    receiving user-determined electrode combination selection criteria from a user, and storing the user-determined electrode combination selection criteria;
    evaluating, for each electrode combination of a plurality of electrode combinations of the plurality of cardiac electrodes, which electrode combination best satisfies the user-determined electrode combination selection criteria, by delivering electrical stimulation to the patient's heart using each electrode combination of the plurality of electrode combinations;

selecting the electrode combination that best satisfies the user-determined electrode combination selection criteria; and deliver a cardiac pacing therapy to the patient's heart that uses the selected electrode combination.

14. The method of claim 13, further comprising:
detecting a condition that triggers an electrode combination update;
repeating the evaluating and selecting steps in response to detecting the condition.

15. The method of claim 14, wherein the condition comprises one or more of loss of capture, change in posture, change in disease state, detection of non-therapeutic activation, and change in patient activity.

16. The method of claim 13, further determining a ranking for at least some of the electrode combinations of the plurality of electrode combinations based on the evaluations of which electrode combination best satisfies the user-determined electrode combination selection criteria.

17. The method of claim 13, further comprising automatically selecting the electrode combination that best satisfies the user-determined electrode combination selection criteria.

18. A method comprising:
delivering electrical stimulation to a patient's heart using a plurality of cardiac electrodes supported inside the patient;
receiving user-determined electrode combination selection criteria from a user via a user interface, and storing the user-determined electrode combination selection criteria in a memory;
identifying, for each electrode combination of a plurality of electrode combinations of the plurality of cardiac electrodes, one or more electrode combinations that are not supportive of cardiac function consistent with the prescribed therapy by delivering electrical stimulation to the patient's heart using each electrode combination, resulting in one or more non-supportive electrode combinations;
for each of the plurality of electrode combinations that are not identified as non-supportive electrode combinations, evaluating which of the electrode combination(s) satisfy the user-determined electrode combination selection criteria;
selecting an electrode combination that satisfies the user-determined electrode combination selection criteria; and
programming an implantable pacing circuit to deliver a cardiac pacing therapy to the patient's heart that uses the selected electrode combination.

19. The method of claim 18, wherein the user-determined electrode combination selection criteria comprises a capture threshold.

20. The method of claim 19, wherein an electrode combination is not supportive of cardiac function consistent with the prescribed therapy if it results in extra-cardiac stimulation of one or more of a nerve or a muscle.

* * * * *